US009393435B2

(12) United States Patent
Mashiach

(10) Patent No.: US 9,393,435 B2
(45) Date of Patent: Jul. 19, 2016

(54) INSERT TOOL FOR SELECTIVELY POWERING AN IMPLANT UNIT

(71) Applicant: Adi Mashiach, Tel Aviv (IL)

(72) Inventor: Adi Mashiach, Tel Aviv (IL)

(*) Notice: Subject to any disclaimer, the term of this patent is extended or adjusted under 35 U.S.C. 154(b) by 0 days.

(21) Appl. No.: 14/519,663

(22) Filed: Oct. 21, 2014

(65) Prior Publication Data
US 2015/0039056 A1 Feb. 5, 2015

Related U.S. Application Data

(62) Division of application No. 13/952,031, filed on Jul. 26, 2013, now Pat. No. 8,897,880.

(60) Provisional application No. 61/676,327, filed on Jul. 26, 2012.

(51) Int. Cl.
*A61N 1/378* (2006.01)
*A61N 1/05* (2006.01)
*A61B 17/04* (2006.01)
(Continued)

(52) U.S. Cl.
CPC .......... *A61N 1/3787* (2013.01); *A61B 17/0482* (2013.01); *A61N 1/0526* (2013.01); *A61N 1/0548* (2013.01); *A61N 1/0558* (2013.01); *A61N 1/3601* (2013.01); *A61N 1/36003* (2013.01); *A61N 1/3605* (2013.01); *A61N 1/3606* (2013.01); *A61N 1/3611* (2013.01); *A61N 1/36071* (2013.01); *A61N 1/36075* (2013.01); *A61N 1/36117* (2013.01); *A61N 1/36125* (2013.01); *A61N 1/36132* (2013.01); *A61N 1/36189* (2013.01); *A61N 1/375* (2013.01); *A61N 1/37229* (2013.01); *H02J 7/025* (2013.01); *H04B 5/0037* (2013.01); *H04B 5/0031* (2013.01); *H04B 5/0081* (2013.01); *H04B 5/0093* (2013.01); *Y10T 29/49018* (2015.01)

(58) Field of Classification Search
CPC . A61N 1/3601; A61N 1/3611; A61N 1/3787; A61N 1/0551; A61N 1/0553; A61N 1/3605; A61N 1/3606; A61B 5/4818; A61B 5/0031
USPC .................................. 607/42, 44, 46, 62, 116
See application file for complete search history.

(56) References Cited

U.S. PATENT DOCUMENTS 4,103,690 A 8/1978 Harris
5,472,438 A 12/1995 Schmit et al.
(Continued)

OTHER PUBLICATIONS

PCT International Search Report and Written Opinion for International Application No. PCT/IB13/02068, dated Feb. 21, 2014 (9 pgs.).

(Continued)

*Primary Examiner* — Rex R Holmes
(74) *Attorney, Agent, or Firm* — Finnegan, Henderson, Farabow, Garrett & Dunner, LLP

(57) ABSTRACT

An implant unit delivery tool is disclosed having an implant tool and an implant activator. The implant tool may be configured to retain an implant unit during an implantation procedure in which the implant unit is fixated to tissue. The implant activator may be associated with the implant tool. Additionally, the implant activator may be configured to selectively transfer power to the implant unit during the implantation procedure to cause modulation of at least one nerve in the body of a subject prior to final fixation of the implant unit to the tissue.

10 Claims, 17 Drawing Sheets

(51) Int. Cl.
*A61N 1/36* (2006.01)
*A61N 1/372* (2006.01)
*H04B 5/00* (2006.01)
*H02J 7/02* (2016.01)
*A61N 1/375* (2006.01)

(56) References Cited

U.S. PATENT DOCUMENTS

| | | | |
|---|---|---|---|
| 5,484,404 | A | 1/1996 | Schulman et al. |
| 6,934,589 | B2 | 8/2005 | Sundquist et al. |
| 7,277,749 | B2 | 10/2007 | Gordon et al. |
| 7,763,034 | B2 | 7/2010 | Siegel et al. |
| 7,799,037 | B1 | 9/2010 | He et al. |
| 2004/0153127 | A1 | 8/2004 | Gordon et al. |
| 2004/0215287 | A1 | 10/2004 | Swoyer et al. |
| 2005/0065545 | A1 | 3/2005 | Wallace |
| 2005/0075681 | A1 | 4/2005 | Rezai et al. |
| 2006/0089633 | A1 | 4/2006 | Bleich et al. |
| 2006/0206164 | A1 | 9/2006 | Gavronsky |
| 2007/0173900 | A1* | 7/2007 | Siegel et al. ............ 607/41 |
| 2007/0296310 | A1 | 12/2007 | Kim et al. |
| 2008/0269716 | A1 | 10/2008 | Bonde et al. |
| 2009/0281503 | A1 | 11/2009 | Lampropoulos |
| 2011/0112610 | A1 | 5/2011 | Rahman et al. |
| 2011/0160557 | A1 | 6/2011 | Cinbis et al. |
| 2011/0160824 | A1 | 6/2011 | Ware et al. |
| 2012/0022580 | A1 | 1/2012 | McCartney |
| 2012/0041512 | A1 | 2/2012 | Weiner |
| 2012/0235634 | A1 | 9/2012 | Hall et al. |
| 2012/0256585 | A1 | 10/2012 | Partovi et al. |
| 2012/0259239 | A1 | 10/2012 | Chenaux et al. |

OTHER PUBLICATIONS

European Search Report for European Application No. 13822575.0, dated Mar. 9, 2016 (5 pages).

* cited by examiner

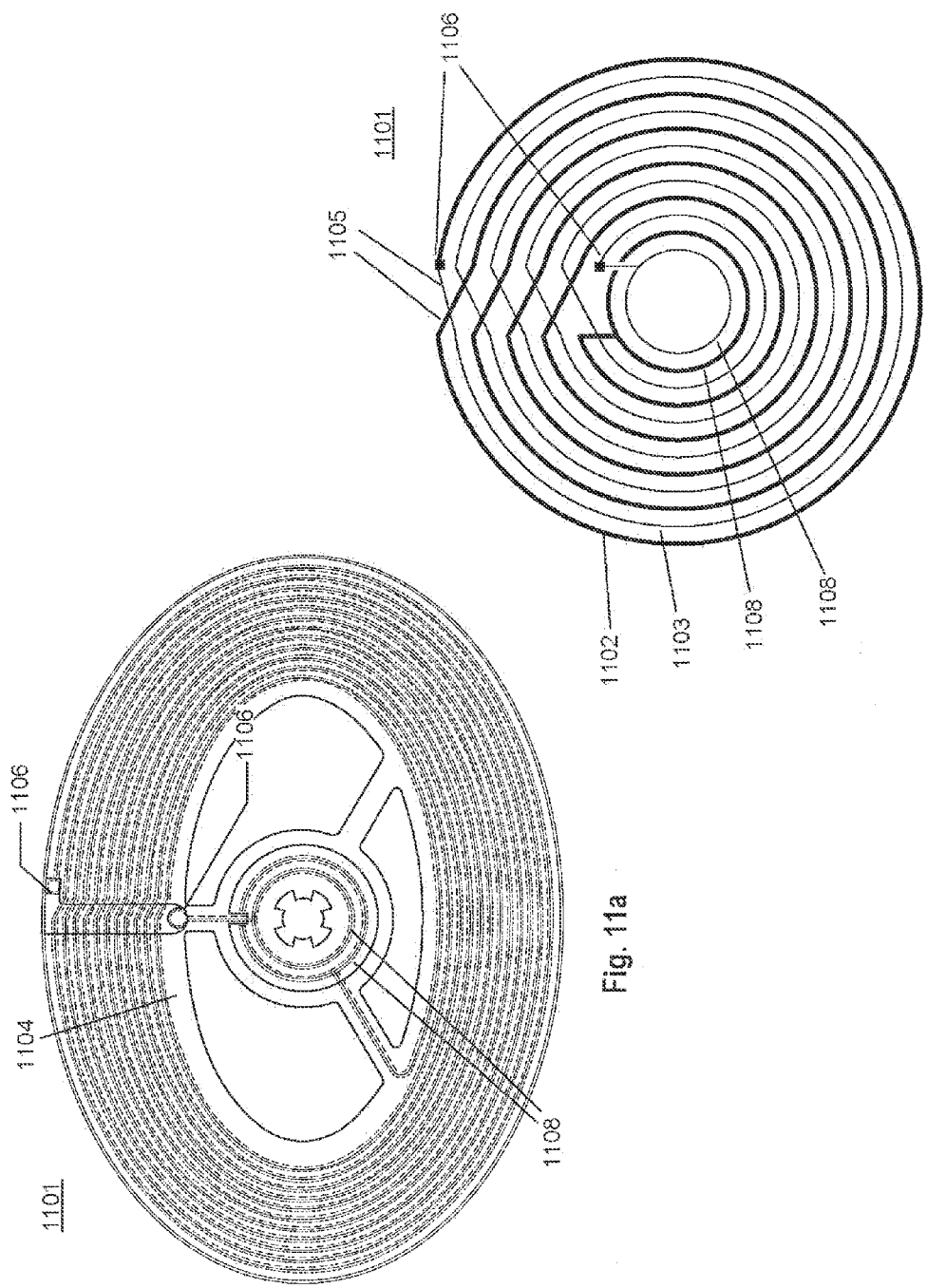

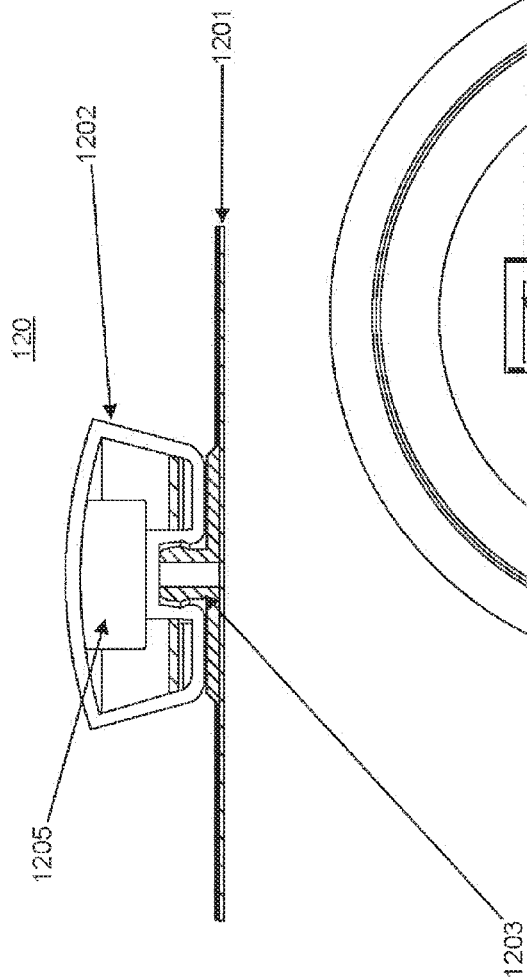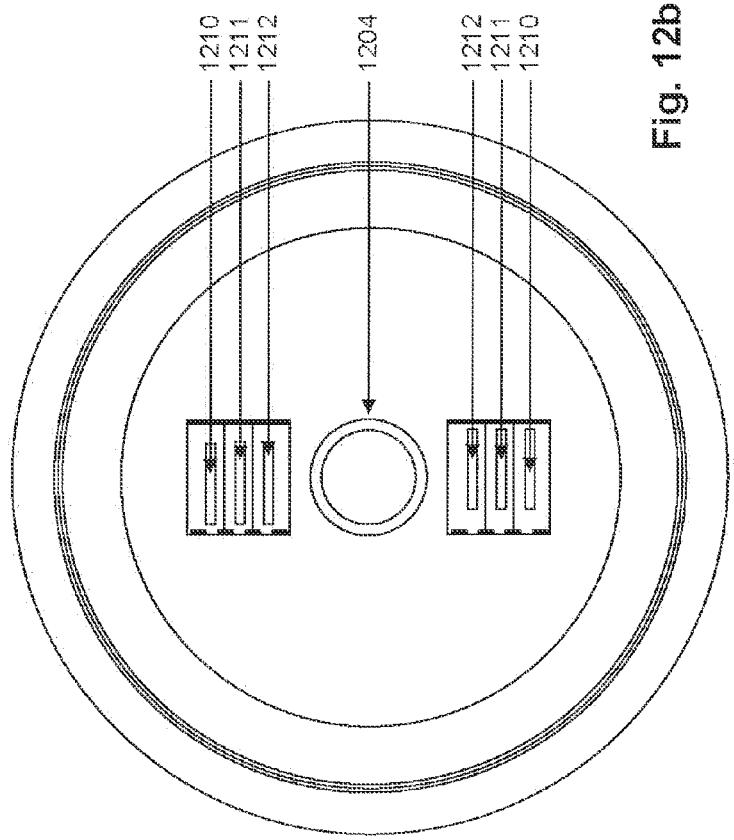

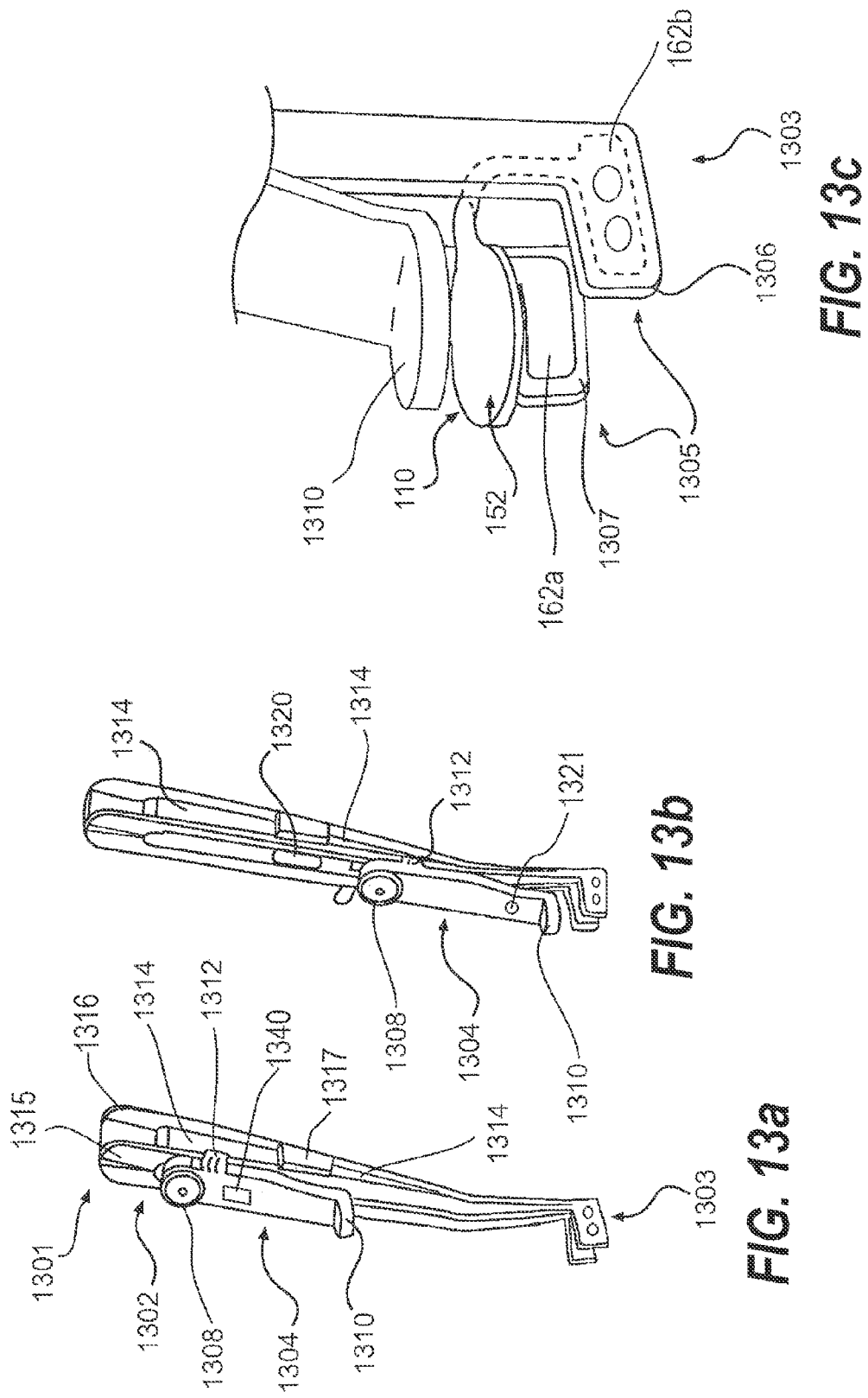

Fig. 16 Modified Class-D Type Amplifier

INSERT TOOL FOR SELECTIVELY POWERING AN IMPLANT UNIT

RELATED APPLICATIONS

This application is a divisional of application Ser. No. 13/952,031, filed Jul. 26, 2013, now U.S. Pat. No. 8,897,880, which claims the benefit of priority under 35 U.S.C. §119(e) to U.S. Provisional Application No. 61/676,327, filed Jul. 26, 2012, each of which is incorporated herein by reference.

TECHNICAL FIELD

Embodiments of the present disclosure generally relate to devices and methods for modulating a nerve. More particularly, embodiments of the present disclosure relate to devices and methods for modulating a nerve through the delivery of energy via an implantable electrical modulator.

BACKGROUND

Neural modulation presents the opportunity to treat many physiological conditions and disorders by interacting with the body's own natural neural processes. Neural modulation includes inhibition (e.g. blockage), stimulation, modification, regulation, or therapeutic alteration of activity, electrical or chemical, in the central, peripheral, or autonomic nervous system. By modulating the activity of the nervous system, for example through the stimulation of nerves or the blockage of nerve signals, several different goals may be achieved. Motor neurons may be stimulated at appropriate times to cause muscle contractions. Sensory neurons may be blocked, for instance to relieve pain, or stimulated, for instance to provide a signal to a subject. In other examples, modulation of the autonomic nervous system may be used to adjust various involuntary physiological parameters, such as heart rate and blood pressure. Neural modulation may provide the opportunity to treat several diseases or physiological conditions, a few examples of which are described in detail below.

Among the conditions to which neural modulation may be applied is obstructive sleep apnea (OSA). OSA is a respiratory disorder characterized by recurrent episodes of partial or complete obstruction of the upper airway during sleep. During the sleep of a person without OSA, the pharyngeal muscles relax during sleep and gradually collapse, narrowing the airway. The airway narrowing limits the effectiveness of the sleeper's breathing, causing a rise in $CO_2$ levels in the blood. The increase in $CO_2$ results in the pharyngeal muscles contracting to open the airway to restore proper breathing. The largest of the pharyngeal muscles responsible for upper airway dilation is the genioglossus muscle, which is one of several different muscles in the tongue. The genioglossus muscle is responsible for forward tongue movement and the stiffening of the anterior pharyngeal wall. In patients with OSA, the neuromuscular activity of the genioglossus muscle is decreased compared to normal individuals, accounting for insufficient response and contraction to open the airway as compared to a normal individual. This lack of response contributes to a partial or total airway obstruction, which significantly limits the effectiveness of the sleeper's breathing. In OSA patients, there are often several airway obstruction events during the night. Because of the obstruction, there is a gradual decrease of oxygen levels in the blood (hypoxemia). Hypoxemia leads to night time arousals, which may be registered by EEG, showing that the brain awakes from any stage of sleep to a short arousal. During the arousal, there is a conscious breath or gasp, which resolves the airway obstruction. An increase in sympathetic tone activity rate through the release of hormones such as epinephrine and noradrenaline also often occurs as a response to hypoxemia. As a result of the increase in sympathetic tone, the heart enlarges in an attempt to pump more blood and increase the blood pressure and heart rate, further arousing the patient. After the resolution of the apnea event, as the patient returns to sleep, the airway collapses again, leading to further arousals.

These repeated arousals, combined with repeated hypoxemia, leaves the patient sleep deprived, which leads to daytime somnolence and worsens cognitive function. This cycle can repeat itself up to hundreds of times per night in severe patients. Thus, the repeated fluctuations in and sympathetic tone and episodes of elevated blood pressure during the night evolve to high blood pressure through the entire day. Subsequently, high blood pressure and increased heart rate may cause other diseases.

Efforts for treating OSA include Continuous Positive Airway Pressure (CPAP) treatment, which requires the patient to wear a mask through which air is blown into the nostrils to keep the airway open. Other treatment options include the implantation of rigid inserts in the soft palate to provide structural support, tracheotomies, or tissue ablation.

Another condition to which neural modulation may be applied is the occurrence of migraine headaches. Pain sensation in the head is transmitted to the brain via the occipital nerve, specifically the greater occipital nerve, and the trigeminal nerve. When a subject experiences head pain, such as during a migraine headache, the inhibition of these nerves may serve to decrease or eliminate the sensation of pain.

Neural modulation may also be applied to hypertension. Blood pressure in the body is controlled via multiple feedback mechanisms. For example, baroreceptors in the carotid body in the carotid artery are sensitive to blood pressure changes within the carotid artery. The baroreceptors generate signals that are conducted to the brain via the glossopharyngeal nerve when blood pressure rises, signaling the brain to activate the body's regulation system to lower blood pressure, e.g. through changes to heart rate, and vasodilation/vasoconstriction. Conversely, parasympathetic nerve fibers on and around the renal arteries generate signals that are carried to the kidneys to initiate actions, such as salt retention and the release of angiotensin, which raise blood pressure. Modulating these nerves may provide the ability to exert some external control over blood pressure.

The foregoing are just a few examples of conditions to which neuromodulation may be of benefit, however embodiments of the invention described hereafter are not necessarily limited to treating only the above-described conditions.

SUMMARY

A implant unit delivery tool, according to some embodiments, may include an implant tool and an implant activator. The implant tool may be configured to retain an implant unit during an implantation procedure in which the implant unit is fixated to tissue. The implant activator may be associated with the implant tool, and configured to selectively transfer power to the implant unit during an implantation procedure to cause modulation of at least one nerve in the body of a subject prior to final fixation of the implant unit to the tissue.

Some embodiments may include a method of testing the functionality of an implant unit. The method may include moving an implant activator from a first position to a second position on a delivery tool, prior to final fixation of an implant unit by the delivery tool. Power may be transferred from the implant activator to the implant unit when the implant activator is in the second position, causing modulation of at least one nerve in the body of a subject.

Additional features of the disclosure will be set forth in part in the description that follows, and in part will be obvious from the description, or may be learned by practice of the disclosed embodiments.

It is to be understood that both the foregoing general description and the following detailed description are exemplary and explanatory only, and are not restrictive of the invention, as claimed.

BRIEF DESCRIPTION OF THE DRAWINGS

The accompanying drawings, which are incorporated in and constitute a part of this specification, illustrate several embodiments of the disclosure and, together with the description, serve to explain the principles of the embodiments disclosed herein.

FIGS. 11a and 11b illustrate a double-layer crossover antenna.

FIGS. 12a and 12b illustrate an exemplary embodiment of an external unit.

FIGS. 13a-13c illustrate various aspects of a delivery tool.

DESCRIPTION OF EXEMPLARY EMBODIMENTS

Reference will now be made in detail to exemplary embodiments of the present disclosure, examples of which are illustrated in the accompanying drawings. Wherever possible, the same reference numbers will be used throughout the drawings to refer to the same or like parts.

Embodiments of the present disclosure relate generally to a device for modulating a nerve through the delivery of energy. Nerve modulation, or neural modulation, includes inhibition (e.g. blockage), stimulation, modification, regulation, or therapeutic alteration of activity, electrical or chemical, in the central, peripheral, or autonomic nervous system. Nerve modulation may take the form of nerve stimulation, which may include providing energy to the nerve to create a voltage change sufficient for the nerve to activate, or propagate an electrical signal of its own. Nerve modulation may also take the form of nerve inhibition, which may including providing energy to the nerve sufficient to prevent the nerve from propagating electrical signals. Nerve inhibition may be performed through the constant application of energy, and may also be performed through the application of enough energy to inhibit the function of the nerve for some time after the application. Other forms of neural modulation may modify the function of a nerve, causing a heightened or lessened degree of sensitivity. As referred to herein, modulation of a nerve may include modulation of an entire nerve and/or modulation of a portion of a nerve. For example, modulation of a motor neuron may be performed to affect only those portions of the neuron that are distal of the location to which energy is applied.

In patients with OSA, for example, a primary target response of nerve stimulation may include contraction of a tongue muscle (e.g., the muscle) in order to move the tongue to a position that does not block the patient's airway. In the treatment of migraine headaches, nerve inhibition may be used to reduce or eliminate the sensation of pain. In the treatment of hypertension, neural modulation may be used to increase, decrease, eliminate or otherwise modify nerve signals generated by the body to regulate blood pressure.

While embodiments of the present disclosure may be disclosed for use in patients with specific conditions, the embodiments may be used in conjunction with any patient/portion of a body where nerve modulation may be desired. That is, in addition to use in patients with OSA, migraine headaches, or hypertension, embodiments of the present disclosure may be use in many other areas, including, but not limited to: deep brain stimulation (e.g., treatment of epilepsy, Parkinson's, and depression); cardiac pace-making, stomach muscle stimulation (e.g., treatment of obesity), back pain, incontinence, menstrual pain, and/or any other condition that may be affected by neural modulation.

Figure 1:
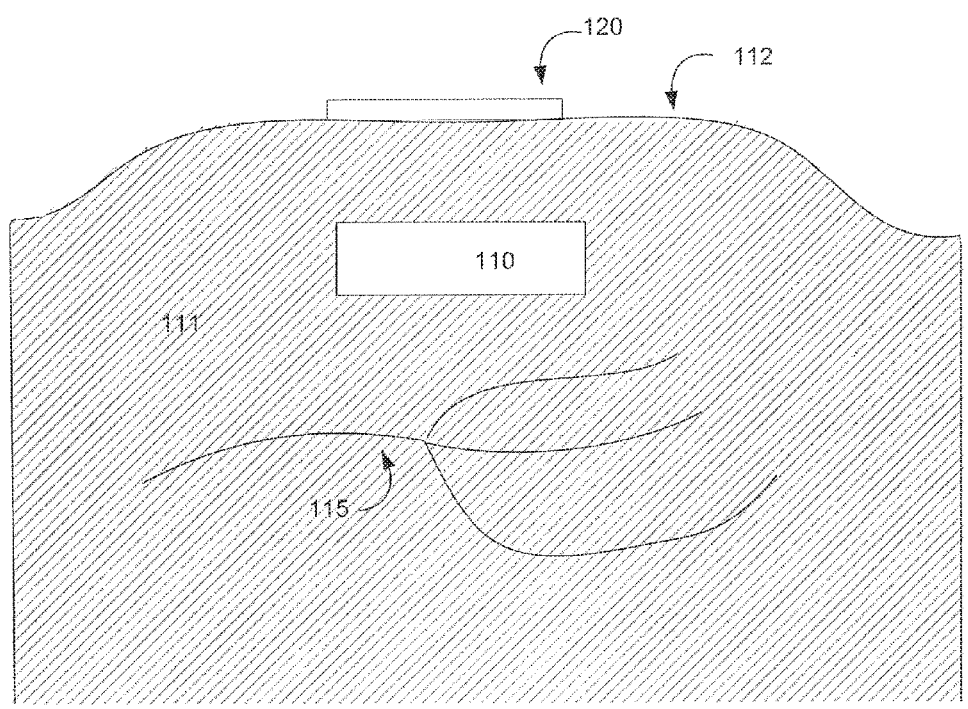
FIG. 1 schematically illustrates an implant unit and external unit, according to an exemplary embodiment of the present disclosure.

FIG. 1 illustrates an implant unit and external unit, according to an exemplary embodiment of the present disclosure. An implant unit 110, may be configured for implantation in a subject, in a location that permits it to modulate a nerve 115. The implant unit 110 may be located in a subject such that intervening tissue 111 exists between the implant unit 110 and the nerve 115. Intervening tissue may include muscle tissue, connective tissue, organ tissue, or any other type of biological tissue. Thus, location of implant unit 110 does not require contact with nerve 115 for effective neuromodulation. The implant unit 110 may also be located directly adjacent to nerve 115, such that no intervening tissue 111 exists.

In treating OSA, implant unit 110 may be located on a genioglossus muscle of a patient. Such a location is suitable for modulation of the hypoglossal nerve, branches of which run inside the genioglossus muscle. Implant unit 110 may also be configured for placement in other locations. For example, migraine treatment may require subcutaneous implantation in the back of the neck, near the hairline of a subject, or behind the ear of a subject, to modulate the greater occipital nerve and/or the trigeminal nerve. Treating hypertension may require the implantation of a neuromodulation implant intravascularly inside the renal artery or renal vein (to modulate the parasympathetic renal nerves), either unilaterally or bilaterally, inside the carotid artery or jugular vein (to modulate the glossopharyngeal nerve through the carotid baroreceptors). Alternatively or additionally, treating hypertension may require the implantation of a neuromodulation implant subcutaneously, behind the ear or in the neck, for example, to directly modulate the glossopharyngeal nerve.

External unit 120 may be configured for location external to a patient, either directly contacting, or close to the skin 112 of the patient. External unit 120 may be configured to be affixed to the patient, for example, by adhering to the skin 112 of the patient, or through a band or other device configured to hold external unit 120 in place. Adherence to the skin of external unit 120 may occur such that it is in the vicinity of the location of implant unit 110.

Figure 2:
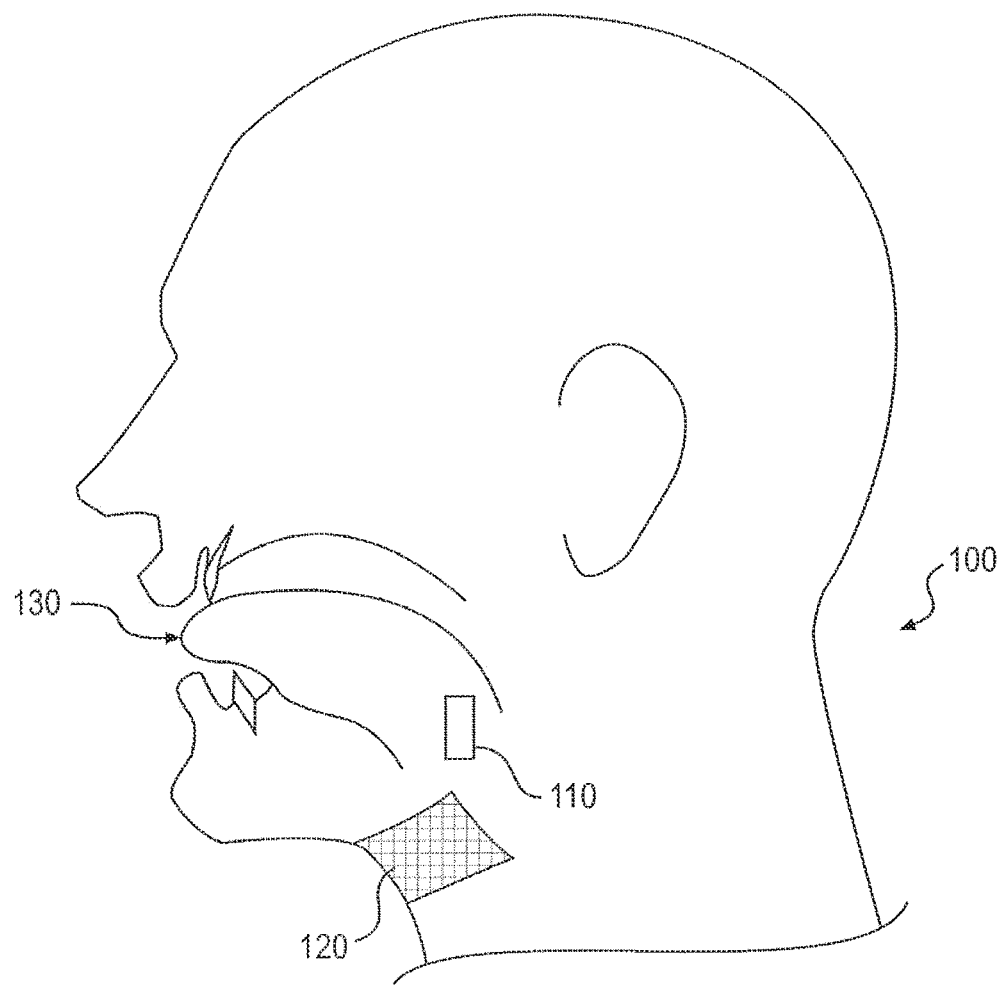
FIG. 2 is a partially cross-sectioned side view of a subject with an implant unit and external unit, according to an exemplary embodiment of the present disclosure.

FIG. 2 illustrates an exemplary embodiment of a neuromodulation system for delivering energy in a patient 100 with OSA. The system may include an external unit 120 that may be configured for location external to the patient. As illustrated in FIG. 2, external unit 120 may be configured to be affixed to the patient 100. FIG. 2 illustrates that in a patient 100 with OSA, the external unit 120 may be configured for placement underneath the patient's chin and/or on the front of patient's neck. The suitability of placement locations may be determined by communication between external unit 120 and implant unit 110, discussed in greater detail below. In alternate embodiments, for the treatment of conditions other than OSA, the external unit may be configured to be affixed anywhere suitable on a patient, such as the back of a patient's neck, i.e. for communication with a migraine treatment implant unit, on the outer portion of a patient's abdomen, i.e. for communication with a stomach modulating implant unit, on a patient's back, i.e. for communication with a renal artery modulating implant unit, and/or on any other suitable external location on a patient's skin, depending on the requirements of a particular application.

External unit 120 may further be configured to be affixed to an alternative location proximate to the patient. For example, in one embodiment, the external unit may be configured to fixedly or removably adhere to a strap or a band that may be configured to wrap around a part of a patient's body. Alternatively, or in addition, the external unit may be configured to remain in a desired location external to the patient's body without adhering to that location.

The external unit 120 may include a housing. The housing may include any suitable container configured for retaining components. In addition, while the external unit is illustrated schematically in FIG. 2, the housing may be any suitable size and/or shape and may be rigid or flexible. Non-limiting examples of housings for the external unit 100 include one or more of patches, buttons, or other receptacles having varying shapes and dimensions and constructed of any suitable material. In one embodiment, for example, the housing may include a flexible material such that the external unit may be configured to conform to a desired location. For example, as illustrated in FIG. 2, the external unit may include a skin patch, which, in turn, may include a flexible substrate. The material of the flexible substrate may include, but is not limited to, plastic, silicone, woven natural fibers, and other suitable polymers, copolymers, and combinations thereof. Any portion of external unit 120 may be flexible or rigid, depending on the requirements of a particular application.

As previously discussed, in some embodiments external unit 120 may be configured to adhere to a desired location. Accordingly, in some embodiments, at least one side of the housing may include an adhesive material. The adhesive material may include a biocompatible material and may allow for a patient to adhere the external unit to the desired location and remove the external unit upon completion of use. The adhesive may be configured for single or multiple uses of the external unit. Suitable adhesive materials may include, but are not limited to biocompatible glues, starches, elastomers, thermoplastics, and emulsions.

Figure 3:
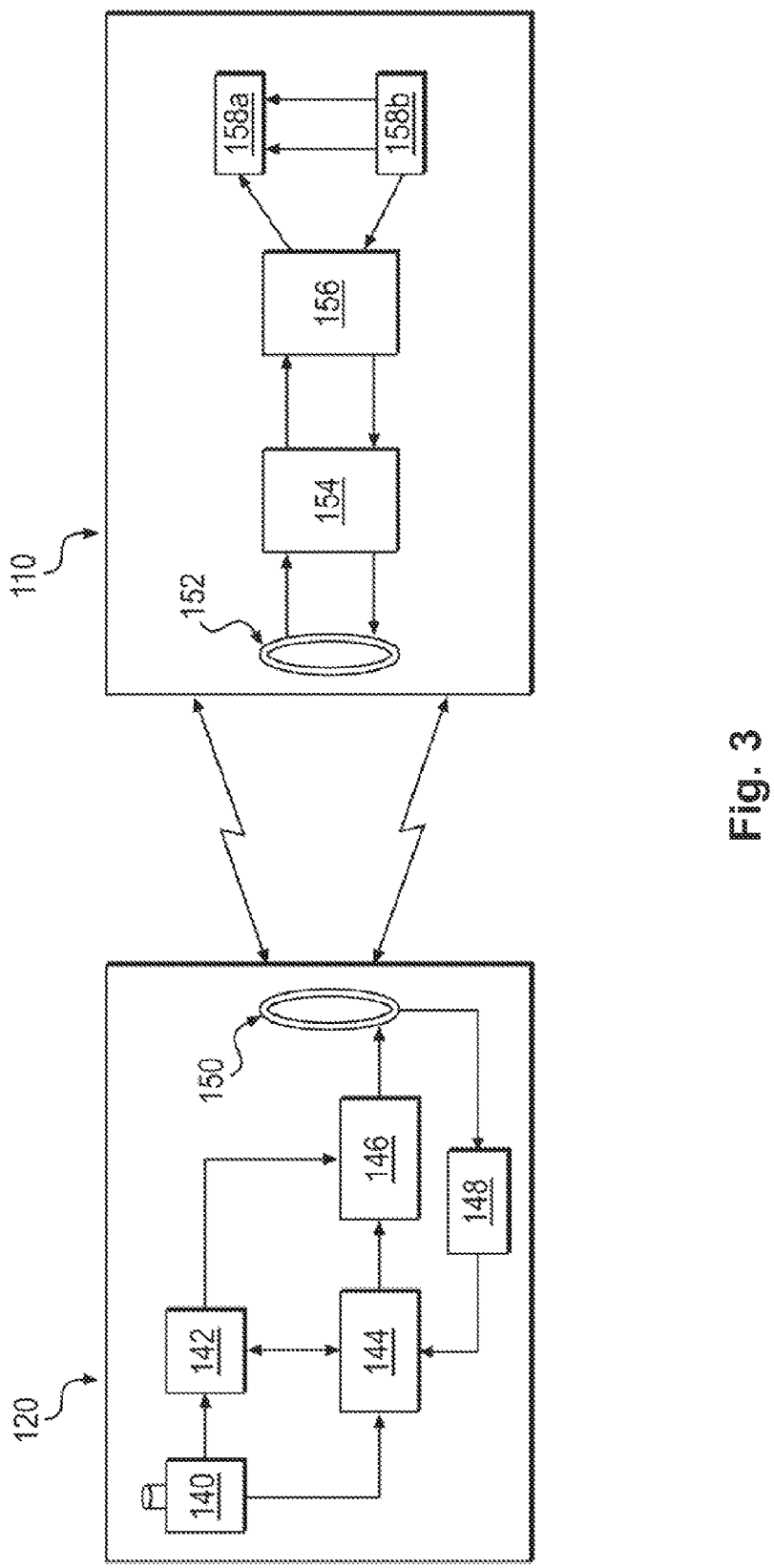
FIG. 3 schematically illustrates a system including an implant unit and an external unit, according to an exemplary embodiment of the present disclosure.

FIG. 3 schematically illustrates a system including external unit 120 and an implant unit 110. In some embodiments, internal unit 110 may be configured as a unit to be implanted into the body of a patient, and external unit 120 may be configured to send signals to and/or receive signals from implant unit 110.

As shown in FIG. 3, various components may be included within a housing of external unit 120 or otherwise associated with external unit 120. As illustrated in FIG. 3, at least one processor 144 may be associated with external unit 120. For example, the at least one processor 144 may be located within the housing of external unit 120. In alternative embodiments, the at least one processor may be configured for wired or wireless communication with the external unit from a location external to the housing.

The at least one processor may include any electric circuit that may be configured to perform a logic operation on at least one input variable. The at least one processor may therefore include one or more integrated circuits, microchips, microcontrollers, and microprocessors, which may be all or part of a central processing unit (CPU), a digital signal processor (DSP), a field programmable gate array (FPGA), or any other circuit known to those skilled in the art that may be suitable for executing instructions or performing logic operations.

FIG. 3 illustrates that the external unit 120 may further be associated with a power source 140. The power source may be removably couplable to the external unit at an exterior location relative to external unit. Alternatively, as shown in FIG. 3, power source 140 may be permanently or removably coupled to a location within external unit 120. The power source may further include any suitable source of power configured to be in electrical communication with the processor. In one embodiment, for example the power source 140 may include a battery.

The power source may be configured to power various components within the external unit 120. As illustrated in FIG. 3, power source 140 may be configured to provide power to the processor 144. In addition, the power source 140 may be configured to provide power to a signal source 142 and a feedback circuit 148. The signal source 142 may be in communication with the processor 144 and may include any device configured to generate a signal (e.g., a sinusoidal signal, square wave, triangle wave, microwave, radio-frequency (RF) signal, or any other type of electromagnetic signal). Signal source 142 may include, but is not limited to, a waveform generator that may be configured to generate alternating current (AC) signals and/or direct current (DC) signals. In one embodiment, for example, signal source 142 may be configured to generate an AC signal for transmission to one or more other components. Signal source 142 may be configured to generate a signal of any suitable frequency. In some embodiments, signal source 142 may be configured to generate a signal having a frequency of from about 6.5 MHz to about 13.6 MHz. In additional embodiments, signal source 142 may be configured to generate a signal having a frequency of from about 7.4 to about 8.8 MHz. In further embodiments, signal source 142 may generate a signal having a frequency as low as 90 kHz or as high as 28 MHz.

Signal source 142 may be configured for direct or indirect electrical communication with an amplifier 146. The amplifier may include any suitable device configured to amplify one or more signals generated from signal source 142. Amplifier 146 may include one or more of various types of amplification devices, including, for example, transistor based devices, operational amplifiers, RF amplifiers, power amplifiers, or any other type of device that can increase the gain associated with one or more aspects of a signal. The amplifier may further be configured to output the amplified signals to one or more components within external unit 120.

Feedback circuit 148, as shown in FIG. 3, may be in communication with various components of external unit 120. For example, feedback circuit 148 may be in direct or indirect electrical contact with processor 144 and a primary antenna 150. In some embodiments, feedback circuit 148 may include, for example, a signal analyzer or a detector.

The external unit 120 may additionally include primary antenna 150. As shown in FIG. 2, primary antenna 150 may be configured as part of a circuit within external unit 120 and may be coupled either directly or indirectly to various components in external unit 120. For example, as shown in FIG. 3, primary antenna 150 may be configured for communication with the amplifier 146.

The primary antenna 150 may include any conductive structure that may be configured to create an electromagnetic field. The primary antenna 150 may further be of any suitable size, shape, and/or configuration. The size, shape, and/or configuration may be determined by the size of the patient, the placement location of the implant unit, the size and/or shape of the implant unit, the amount of energy required to modulate a nerve, a location of a nerve to be modulated, the type of receiving electronics present on the implant unit, etc. The primary antenna may include any suitable antenna known to those skilled in the art that may be configured to send and/or receive signals. Suitable antennas may include, but are not limited to, a long-wire antenna, a patch antenna, a helical antenna, etc. In one embodiment, for example, as illustrated in FIG. 3, primary antenna 150 may include a coil antenna. Such a coil antenna may be made from any suitable conductive material and may be configured to include any suitable arrangement of conductive coils (e.g., diameter, number of coils, layout of coils, etc.). A coil antenna suitable for use as primary antenna 150 may have a diameter of between about 1 cm and 10 cm, and may be circular or oval shaped. In some embodiments, a coil antenna may have a diameter between 5 cm and 7 cm, and may be oval shaped. A coil antenna suitable for use as primary antenna 150 may have any number of windings, e.g. 4, 8, 12, or more. A coil antenna suitable for use as primary antenna 150 may have a wire diameter between about 0.01 mm and 2 mm. These antenna parameters are exemplary only, and may be adjusted above or below the ranges given to achieve suitable results.

As noted, implant unit 110 may be configured to be implanted in a patient's body (e.g., beneath the patient's skin). FIG. 2 illustrates that the implant unit 110 may be configured to be implanted for modulation of a nerve associated with a muscle of the subject's tongue 130. Modulating a nerve associated with a muscle of the subject's tongue 130 may include stimulation to cause a muscle contraction. In further embodiments, the implant unit may be configured to be placed in conjunction with any nerve that one may desire to modulate. For example, modulation of the occipital nerve, the greater occipital nerve, and/or the trigeminal nerve may be useful for treating pain sensation in the head, such as that from migraines. Modulation of parasympathetic nerve fibers on and around the renal arteries (i.e., the renal nerves), the vagus nerve, and/or the glossopharyngeal nerve may be useful for treating hypertension. Additionally, any nerve of the peripheral nervous system (both spinal and cranial), including motor neurons, sensory neurons, sympathetic neurons and parasympathetic neurons, may be modulated to achieve a desired effect.

Implant unit 110 may be formed of any materials suitable for implantation into the body of a patient. In some embodiments, implant unit 110 may include a flexible carrier 161 (FIG. 4) including a flexible, biocompatible material. Such materials may include, for example, silicone, polyimides, phenyltrimethoxysilane (PTMS), polymethyl methacrylate (PMMA), Parylene C, polyimide, liquid polyimide, laminated polyimide, black epoxy, polyether ether ketone (PEEK), Liquid Crystal Polymer (LCP), Kapton, etc. Implant unit 110 may further include circuitry including conductive materials, such as gold, platinum, titanium, or any other biocompatible conductive material or combination of materials. Implant unit 110 and flexible carrier 161 may also be fabricated with a thickness suitable for implantation under a patient's skin. Implant 110 may have thickness of less than about 4 mm or less than about 2 mm. Other components that may be included in or otherwise associated with the implant unit are illustrated in FIG. 3. Similar to the primary antenna 150, the secondary antenna 152 may include any suitable antenna known to those skilled in the art that may be configured to send and/or receive signals. The secondary antenna may include any suitable size, shape, and/or configuration. The size, shape and/or configuration may be determined by the size of the patient, the placement location of the implant unit, the amount of energy required to modulate the nerve, etc. Suitable antennas may include, but are not limited to, a long-wire antenna, a patch antenna, a helical antenna, etc. In some embodiments, for example, secondary antenna 152 may include a coil antenna having a circular shape (see also FIG. 4) or oval shape. Such a coil antenna may be made from any suitable conductive material and may be configured to include any suitable arrangement of conductive coils (e.g., diameter, number of coils, layout of coils, etc.). A coil antenna suitable for use as secondary antenna 152 may have a diameter of between about 5 mm and 30 mm, and may be circular or oval shaped. A coil antenna suitable for use as secondary antenna 152 may have any number of windings, e.g. 4, 15, 20, 30, or 50. A coil antenna suitable for use as secondary antenna 152 may have a wire diameter between about 0.001 mm and 1 mm. These antenna parameters are exemplary only, and may be adjusted above or below the ranges given to achieve suitable results. FIGS. 11a and 11b illustrate a double-layer crossover antenna 1101 suitable for use as either primary antenna 150 or secondary antenna 152. While a double-layer crossover antenna is shown and described, other antenna configurations may be suitable for primary antenna 150 and/or secondary antenna 152. For example, single layer antennas may be used where antenna components (e.g., coils) are arranged in a single layer, e.g., either on or within a dielectric or insulating material. Also, while a crossover pattern is shown, other patterns may also be suitable. For example, in some embodiments, a wire associated with primary antenna 150 and/or secondary antenna 152 may include a pattern of traces of progressively decreasing dimension. In the case of traces arranged in coils, for example, each loop may include rings of progressively decreasing diameter to create a pattern that spirals inwardly. A similar approach may be viable using traces of other shapes as well.

Returning to FIG. 11a, this figure illustrates a single coil of double-layer crossover antenna 1101, while FIG. 11b illustrates two layers of double layer crossover antenna 1101. Antenna 1101 may include a first coil of wire 1102 arranged on a first side of a dielectric carrier 1104 and a second coil of wire 1103 on a second side of a dielectric carrier 1104.

Arranging the antenna coils in a double layer may serve to increase the transmission range of the antenna without increasing the size of the antenna. Such an arrangement, however, may also serve to increase capacitance between the wires of each coil. In each wire coil, an amount of parasitic capacitance between wires may partially depend on the distance each wire is from its neighbor. In a single layer coil, capacitance may be generated between each loop of the coil and its neighbors to either side. Thus, more compact coils may generate more parasitic capacitance. When a second layer coil is added, additional capacitance may then be generated between the wires of the first coil and the wires of the second coil. This additional capacitance may be further increased if corresponding loops of the first and second coils have the same or similar diameters, and/or if a dielectric carrier separating the loops is made very thin. Increased parasitic capacitance in an antenna may serve to alter characteristics, such as resonant frequency, of the antenna in unpredictable amounts based on manufacturing specifications. Additionally, resonant frequency drift, caused for example by moisture incursion or antenna flexing, may be increased by the presence of increased parasitic capacitance. Thus, in order to decrease variability in the manufactured product, it may be advantageous to reduce the levels of parasitic capacitance in a dual layer antenna.

FIG. 11b illustrates a double layer crossover antenna 1101 which may serve to reduce the parasitic capacitance in a manufactured antenna. As illustrated in FIG. 11b, a first coil of wire 1102 is concentrically offset from a second coil of wire 1103. In contrast to a configuration where each loop of a first coil 1102 has the same diameter as corresponding loop of the second coil 1103, concentrically offsetting corresponding loops of each wire coil serves to increase the distance between a single loop of the first coil 1102 with a corresponding loop of the second coil 1103. This increased distance, in turn, may decrease the parasitic wire-to-wire capacitance between loops of first coil 1102 and corresponding loops of second coil 1103. This configuration may be particularly advantageous in reducing parasitic capacitance in a situation where a dielectric carrier 1104 is thin enough such that the concentric distance by which each coil is offset is relatively large compared to the thickness of the dielectric carrier 1104. For example, in a situation where a dielectric carrier is 0.5 mm thick, a concentric offset of 0.5 mm or more may produce a large change in parasitic capacitance. In contrast, in a situation where a dielectric carrier is 5 mm thick, a concentric offset of 0.5 mm may produce a smaller change in parasitic capacitance. The concentric offset between a first coil 1102 and a second coil 1103 may be achieved, for example, by a plurality of electrical trace steps 1105 that offset each loop of the coils from each preceding loop. Electrical trace steps 1105 on a first side of dielectric carrier 1104 cross over electrical trace steps 1105 on a second side of dielectric carrier 1104, thus providing the crossover feature of double-layer crossover antenna 1101.

In additional embodiments, double layer crossover antenna 1101 may include openings 1106 in dielectric carrier 1104 to facilitate the electrical connection of first and second coils 1102, 1103. First and second coils 1102, 1103 of double layer crossover antenna 1101 may also include exposed electrical portions 1108 configured to electrically connect with a connector of a device housing that may be coupled to antenna 1101. Exposed electrical portions 1108 may be configured so as to maintain electrical contact with the connector of a device housing independent of the axial orientation of the connection. As shown in FIG. 11a, for example, exposed electrical portions 1108 may be configured as continuous or discontinuous circles in order to achieve this. A first exposed electrical portion 1108 configured as a discontinuous circle may provide a space through which an electrical trace may pass without contacting the first exposed electrical portion, for example to connect with a second exposed electrical portion located inside the first, or to other components located within the circle of the first exposed electrical portion 1108. FIG. 11a illustrates an antenna having substantially elliptical coils; other shapes, such as circular, triangular, square, etc., may be also be used in different embodiments. Elliptical coils may facilitate placement of external unit 120 in certain areas (e.g., under the chin of a subject) while maintaining desirable electrical performance characteristics. FIGS. 12a and 12b illustrate an exemplary embodiment of external unit 120, including features that may be found in any combination in other embodiments. FIG. 12a illustrates a side view of external unit 120, depicting carrier 1201 and electronics housing 1202.

Carrier 1201 may include a skin patch configured for adherence to the skin of a subject, for example through adhesives of mechanical means. Carrier 1201 may be flexible or rigid, or may have flexible portions and rigid portions. Carrier 1201 and may include primary antenna 150, for example, a double-layer crossover antenna 1101 such as that illustrated in FIGS. 11a and 11b. Carrier 1201 may also include power source 140, such as a paper battery, thin film battery, or other type of substantially flat and/or flexible battery. Carrier 1201 may also include any other type of battery or power source. Carrier 1201 may also include a connector 1203 configured for selectively or removably connecting carrier 1201 to electronics housing 1202. Connector 1203 may extend or protrude from carrier 1201. Connector 1203 may be configured to be received by a recess 1204 of electronics housing 1202 Connector 1203 may be configured as a non-pouch connector, configured to provide a selective connection to electronics housing 1204 without the substantial use of concave feature. Connector 1203 may include, for example a peg, and may have flexible arms. Connector 1203 may further include a magnetic connection, a velcro connection, and/or a snap dome connection. Connector 1203 may also include a locating feature, configured to locate electronics housing 1202 at a specific height, axial location, and/or axial orientation with respect to carrier 1201. A locating feature of connector 1203 may further include pegs, rings, boxes, ellipses, bumps, etc. Connector 1203 may be centered on carrier 1201, may be offset from the center by a predetermined amount, or may be provided at any other suitable location of carrier 1201. Multiple connectors 1203 may be provided on carrier 1201. Connector 1203 may be configured such that removal from electronics housing 1202 causes breakage of connector 1203. Such a feature may be desirable to prevent re-use of carrier 1201, which may lose some efficacy through continued use.

Figure 6:
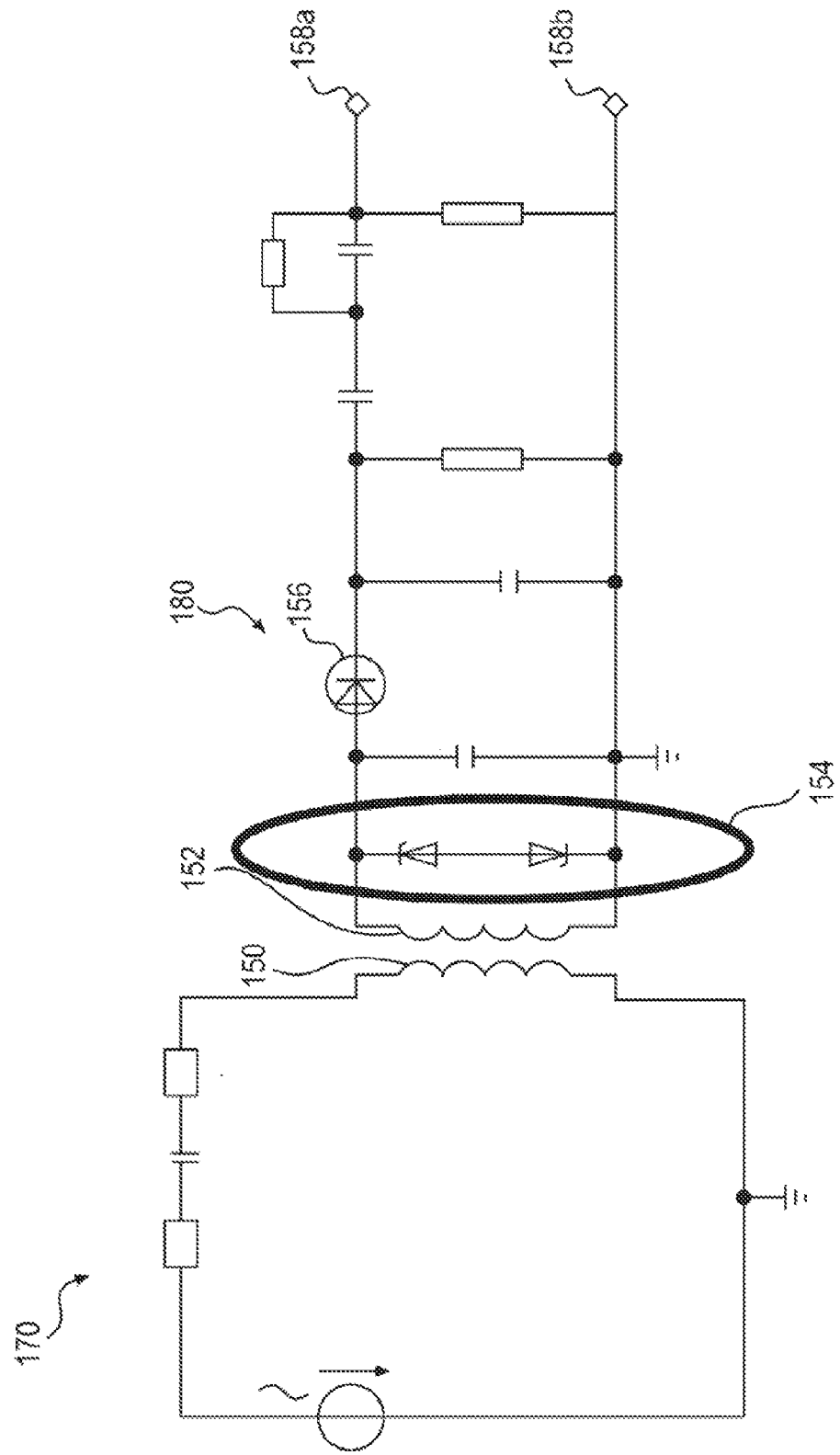
FIG. 6 illustrates circuitry of an implant unit and an external unit, according to an exemplary embodiment of the present disclosure.

Electronics housing 1202 is illustrated in side view in FIG. 12a and in a bottom view in FIG. 12b. Electronics housing 1202 may include electronics portion 1205, which may be arranged inside electronics housing 1202 in any manner that is suitable. Electronics portion 1205 may include various components, further discussed below, of external unit 120. For example, electronics portion 1205 may include any combination of at least one processor 144 associated with external unit 120, power source 140, such as a battery, primary antenna 150, and an electrical circuit 170 (as shown in FIG. 6). Electronics portion 1205 may also include any other component described herein as associated with external unit 120. Additional components may also be recognized by those of skill in the art.

Electronics housing 1202 may include recess 1204 configured to receive connector 1203. Electronics housing 1202 may include at least one electrical connector 1210, 1211, 1212. Electrical connectors 1210, 1211, 1212 may be arranged with pairs of electrical contacts, as shown in FIG. 12b, or with any other number of electrical contacts. The pair of electrical contacts of each electrical connector 1210, 1211, 1212 may be continuously electrically connected with each other inside of housing 1202, such that the pair of electrical contacts represents a single connection point to a circuit. In such a configuration, it is only necessary that one of the electrical contacts within a pair be connected to the circuit. Electrical connectors 1210, 1211, and 1212 may thus include redundant electrical contacts. The electrical contacts of each electrical connector 1210, 1211, 1212 may also represent opposite ends of a circuit, for example, the positive and negative ends of a battery charging circuit. In an exemplary embodiment, as shown in FIG. 12b, electrical connectors 1210, 1211, and 1212 are configured so as to maintain electrical contact with an exposed electrical portion 1108 independent of an axial orientation of electronics housing 1202. Connection between any or all of electrical connectors 1210, 1211, 1212 and exposed electrical portions 1108 may thus be established and maintained irrespective of relative axial positions of carrier 1201 and housing 1202. Thus, when connector 1203 is received by recess 1204, housing 1202 may rotate with respect to carrier 1201 without interrupting electrical contact between at least one of electrical connectors 1210, 1211, 1212 and exposed electrical portions 1108. Axial orientation independence may be achieved, for example, through the use of circular exposed electrical portions 1108 and each of a pair of contacts of electrical connectors 1210, 1211, 1212 disposed equidistant from a center of recess 1204 at a radius approximately equal to that of a corresponding exposed electrical portion 1108. In this fashion, even if exposed electrical portion 1108 includes a discontinuous circle, at least one electrical contact of electrical connectors 1210, 1211, and 1212 may make contact. In FIG. 12b, electrical connectors 1210, 1211, 1212 are illustrated as pairs of rectangular electrical contacts. Electrical connectors 1210, 1211, 1212, however, may include any number of contacts, be configured as continuous or discontinuous circles, or have any other suitable shape or configuration.

One exemplary embodiment may operate as follows. As shown in FIG. 12b, electronics housing 1202 may include more electrical connectors 1210, 1211, 1212, than a carrier 1201 includes exposed electrical portions 1108. In the illustrated embodiments, electronics housing 1202 includes three electrical connectors 1210, 1211, and 1212, while a double-layer crossover antenna 1101 includes two exposed electrical portions 1108 (FIG. 11a). In such an embodiment, two electrical connectors 1211 and 1212 may be configured with continuously electrically connected electrical contacts, such that each connector makes contact with a different exposed electrical portion 1108, where the exposed electrical portions 1108 represent opposite ends of double layer crossover antenna 1101. Thus, antenna 1101 may be electrically connected to the electrical components contained in electronics portion 1205. When connected to carrier 1201 in this configuration, electrical connectors 1210 may not make contact with any electrodes. In this embodiment, electrical connectors 1210 may be reserved to function as opposite ends of a battery charging circuit, in order to charge a battery contained in electronics portion 1205 when electronics housing 1202 is not being used for therapy. A battery charger unit may be provided with a non-breakable connector similar to that of non-pouch connector 1203, and configured to engage with recess 1204. Upon engaging with recess 1204, electrode contacts of the battery charger unit may contact electrical connectors 1210 to charge a battery contained within electronics portion 1205.

Figure 4:
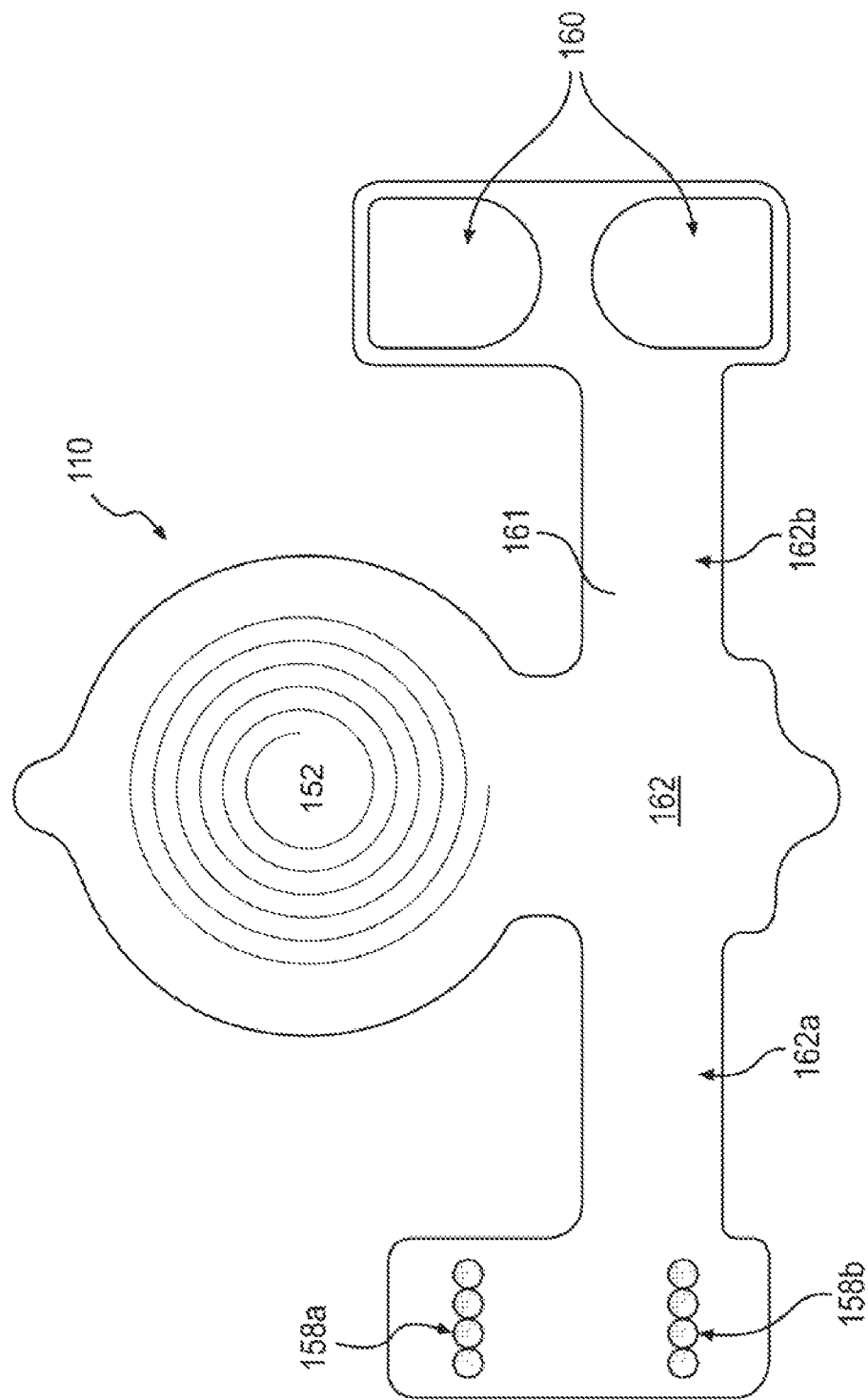
FIG. 4 is a top view of an implant unit, according to an exemplary embodiment of the present disclosure.

In an additional embodiment consistent with the present disclosure, electronics housing 1202 may include an activator chip. Processor 144 may be configured to activate when at least one of electrical connectors 1210, 1211, 1212 contact exposed electrical portions 1108 included in carrier 1201. In this manner, an electronics housing 1202 may be charged and left dormant for many days prior to activation. Simply connecting electronics housing 1202 to carrier 1201 (and inducing contact between an electrical connector 1210, 1211, 1212 and an electrode portion 1108) may cause the processor to activate. Upon activation, processor 144 may be configured to enter a specific mode of operation, such as a calibration mode (for calibrating the processor after placement of the carrier on the skin), a placement mode (for assisting a user to properly place the carrier on the skin), and/or a therapy mode (to begin a therapy session). The various modes of processor 144 may include waiting periods at the beginning, end, or at any time during. For example, a placement mode may include a waiting period at the end of the mode to provide a period during which a subject may fall asleep. A therapy mode may include a similar waiting period at the beginning of the mode. Additionally or alternatively, processor 144 may be configured to provide waiting periods separate from the described modes, in order to provide a desired temporal spacing between system activities. Implant unit 110, as shown in FIG. 3, may additionally include a plurality of field-generating implant electrodes 158a, 158b. The electrodes may include any suitable shape and/or orientation on the implant unit so long as the electrodes may be configured to generate an electric field in the body of a patient. Implant electrodes 158a and 158b may also include any suitable conductive material (e.g., copper, silver, gold, platinum, iridium, platinum-iridium, platinum-gold, conductive polymers, etc.) or combinations of conductive (and/or noble metals) materials. In some embodiments, for example, the electrodes may include short line electrodes, circular electrodes, and/or circular pairs of electrodes. As shown in FIG. 4, electrodes 158a and 158b may be located on an end of a first extension 162a of an elongate arm 162. The electrodes, however, may be located on any portion of implant unit 110. Additionally, implant unit 110 may include electrodes 158a, 158b located at a plurality of locations, for example on an end of both a first extension 162a and a second extension 162b of elongate arm 162, as illustrated, for example, in FIG. 5. Implant electrodes 158a, 158b may have a thickness between about 200 nanometers and 1 millimeter. Anode and cathode electrode pairs of electrodes 158a, 158b may be spaced apart by about a distance of about 0.2 mm to 25 mm. In additional embodiments, anode and cathode electrode pairs may be spaced apart by a distance of about 1 mm to 10 mm, or between 4 mm and 7 mm. Adjacent anodes or adjacent cathodes may be spaced apart by distances as small as 0.001 mm or less, or as great as 25 mm or more. In some embodiments, adjacent anodes or adjacent cathodes may be spaced apart by a distance between about 0.2 mm and 1 mm.

FIG. 4 provides a schematic representation of an exemplary configuration of implant unit 110. As illustrated in FIG. 4, in one embodiment, the field-generating electrodes 158a and 158b may include two sets of four circular electrodes, provided on flexible carrier 161, with one set of electrodes providing an anode and the other set of electrodes providing a cathode. Implant unit 110 may include one or more structural elements to facilitate implantation of implant unit 110 into the body of a patient. Such elements may include, for example, elongated arms, suture holes, polymeric surgical mesh, biological glue, spikes of flexible carrier protruding to anchor to the tissue, spikes of additional biocompatible material for the same purpose, etc. that facilitate alignment of implant unit 110 in a desired orientation within a patient's body and provide attachment points for securing implant unit 110 within a body. For example, in some embodiments, implant unit 110 may include an elongate arm 162 having a first extension 162*a* and, optionally, a second extension 162*b*. Extensions 162*a* and 162*b* may aid in orienting implant unit 110 with respect to a particular muscle (e.g., the genioglossus muscle), a nerve within a patient's body, or a surface within a body above a nerve. For example, first and second extensions 162*a*, 162*b* may be configured to enable the implant unit to conform at least partially around soft or hard tissue (e.g., nerve, bone, or muscle, etc.) beneath a patient's skin. Further, implant unit 110 may also include one or more suture holes 160 located anywhere on flexible carrier 161. For example, in some embodiments, suture holes 160 may be placed on second extension 162*b* of elongate arm 162 and/or on first extension 162*a* of elongate arm 162. Implant unit 110 may be constructed in various shapes. Additionally, or alternatively, implant unit 110 may include surgical mesh 1050 or other perforatable material, described in greater detail below with respect to FIG. 10. In some embodiments, implant unit may appear substantially as illustrated in FIG. 4. In other embodiments, implant unit 110 may lack illustrated structures such as second extension 162*b*, or may have additional or different structures in different orientations. Additionally, implant unit 110 may be formed with a generally triangular, circular, or rectangular shape, as an alternative to the winged shape shown in FIG. 4. In some embodiments, the shape of implant unit 110 (e.g., as shown in FIG. 4) may facilitate orientation of implant unit 110 with respect to a particular nerve to be modulated. Thus, other regular or irregular shapes may be adopted in order to facilitate implantation in differing parts of the body.

Figure 5:
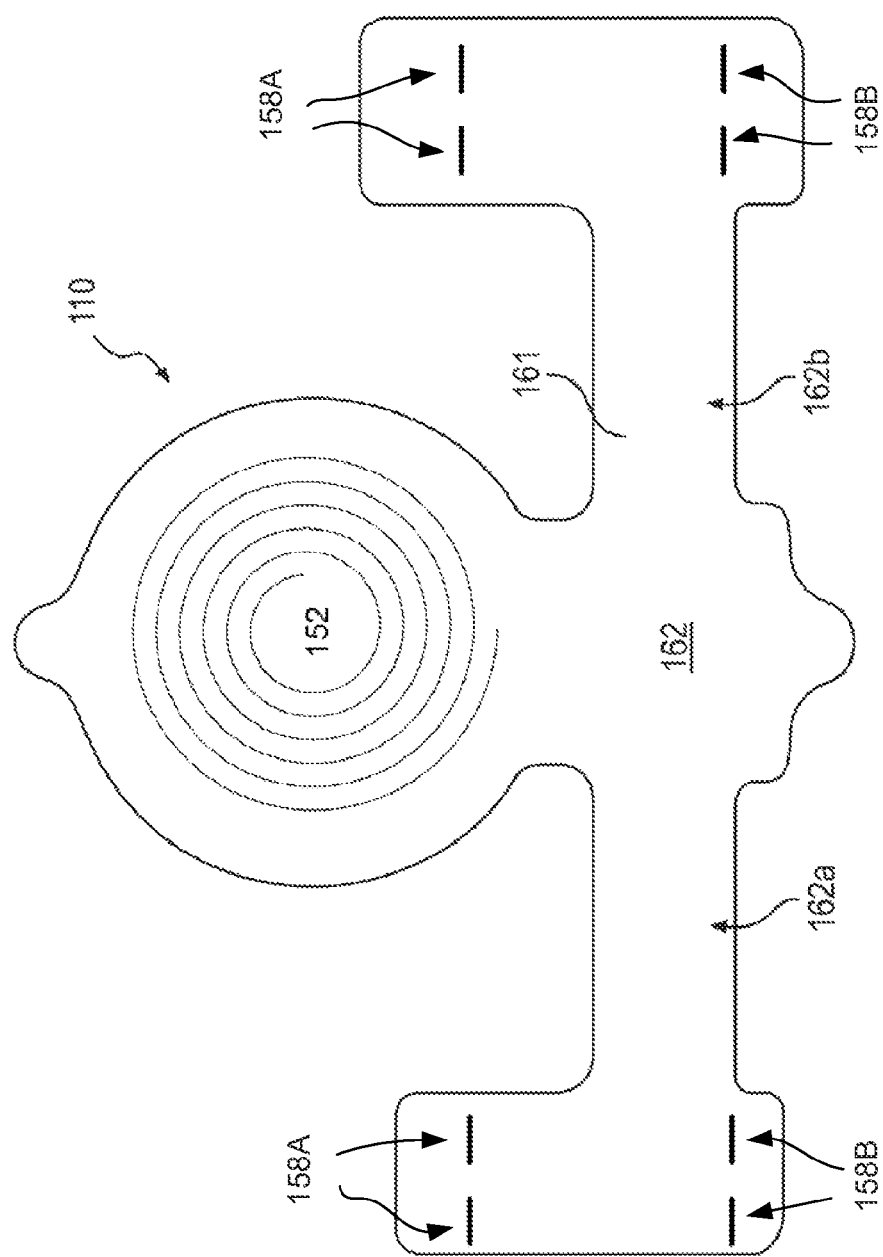
FIG. 5 is a top view of an alternate embodiment of an implant unit, according to an exemplary embodiment of the present disclosure.
Figure 10:
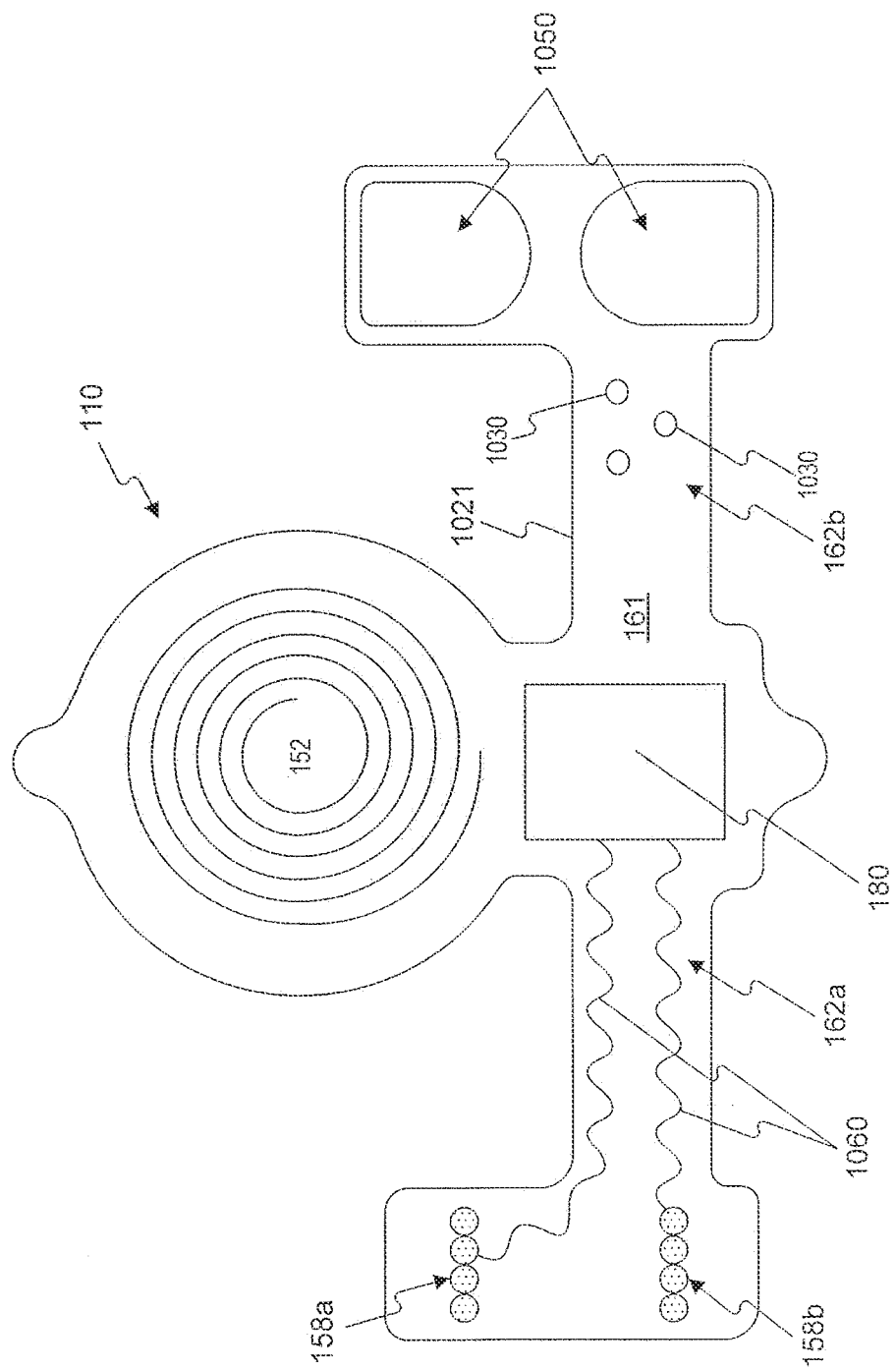
FIG. 10 illustrates additional features of one embodiment of implant unit 110.

As illustrated in FIG. 4, secondary antenna 152 and electrodes 158*a*, 158*b* may be mounted on or integrated with flexible carrier 161. Various circuit components and connecting wires (discussed further below) may be used to connect secondary antenna with implant electrodes 158*a* and 158*b*. To protect the antenna, electrodes, circuit components, and connecting wires from the environment within a patient's body, implant unit 110 may include a protective coating that encapsulates implant unit 110. In some embodiments, the protective coating may be made from a flexible material to enable bending along with flexible carrier 161. The encapsulation material of the protective coating may also resist humidity penetration and protect against corrosion. In some embodiments, the protective coating may include a plurality of layers, including different materials or combinations of materials in different layers FIG. 5 is a perspective view of an alternate embodiment of an implant unit 110, according to an exemplary embodiment of the present disclosure. As illustrated in FIG. 5, implant unit 110 may include a plurality of electrodes 158*a*, 158*b* located, for example, at the ends of first extension 162*a* and second extension 162*b*. FIG. 5 illustrates an embodiment wherein implant electrodes 158*a* and 158*b* include short line electrodes. FIG. 10 is a photograph illustrating additional features of one embodiment of implant unit 110. Exemplary embodiments may incorporate some or all of the features illustrated in FIG. 10. A protective coating of implant unit 110 may include a primary capsule 1021. Primary capsule 1021 may encapsulate the implant unit 110 and may provide mechanical protection for the implant unit 110. For example, the components of implant unit 110 may be delicate, and the need to handle the implant unit 110 prior to implantation may require additional protection for the components of implant unit 110. Primary capsule 1021 may provide such protection. Primary capsule 1021 may encapsulate all or some of the components of implant unit 110. For example, primary capsule 1021 may encapsulate primary antenna 152, carrier 161, and circuit 180, while leaving electrodes 158*a*, 158*b* exposed. In alternative embodiments, different combinations of components may be encapsulated or exposed. Primary capsule 1021 may be fashioned of a material and thickness such that implant unit 110 remains flexible after encapsulation. Primary capsule 1021 may include any suitable bio-compatible material, such as silicone, or polyimides, phenyltrimethoxysilane (PTMS), polymethyl methacrylate (PMMA), Parylene C, liquid polyimide, laminated polyimide, polyimide, Kapton, black epoxy, polyether ketone (PEEK), Liquid Crystal Polymer (LCP), or any other suitable biocompatible coating.

The protective coating of implant unit 110 may also include a secondary capsule (not shown). A secondary capsule may provide environmental protection for the implant unit 110 when it is implanted in the body. For example, primary capsule 1021, when constructed of silicone, may be subject to moisture incursion from the body, which may limit a life-span of the implant unit 110 due to possible corrosive effects. A secondary capsule may be provided underneath the primary capsule to protect implant unit 110 from the corrosive effects of bodily implantation. For example, a layer of parylene C may serve as a secondary capsule and may be provided to encapsulate all or some of the components of implant unit 110. The secondary capsule may, in turn, be encapsulated by primary capsule 1021. A secondary capsule, may include, for example parylene C or any other suitable material to prevent the effects of moisture incursion on implant unit 110. In some embodiments, a secondary capsule layer may be deposited by chemical vapor deposition and may have a thickness of about 1 molecule in thickness, between 1 and 5 molecules in thickness, or any other suitable film thickness.

Some combinations of primary and secondary capsule materials, such as silicone and parylene C, may bond relatively weakly to one another. Where such combinations of materials are used, a plurality penetrating holes 1030 may be provided to pass through both carrier 161 and a secondary capsule to improve the adherence of the primary capsule. When penetrating holes 1030 are provided, the material of primary capsule 1021 may flow through the penetrating holes, permitting the material of primary capsule 1021 to flow into and adhere to itself. A plurality of penetrating holes 1030 provided through carrier 161 and a secondary capsule may provide a multitude of anchor points to permit a primary capsule 1021 material to self adhere. Penetrating holes 1030 may be provided such that, after encapsulation by primary capsule 1021, the holes 1030 remain, or they may be provided such that, after encapsulation, the holes 1030 are filled in.

Also illustrated in FIG. 10 is encapsulated surgical mesh 1050. Surgical mesh 1050 may provide a larger target area for surgeons to use when suturing implant unit 110 into place during implantation. The entire surgical mesh 1050 may be encapsulated by primary capsule 1021, permitting a surgeon to pass a needle through any portion of the mesh without compromising the integrity of implant unit 110. Surgical mesh 1050 may additionally be used to cover suture holes 160, permitting larger suture holes 160 that may provide surgeons with a greater target area. Surgical mesh 1050 may also encourage surrounding tissue to bond with implant unit 110. In some embodiments, a surgeon may pass a surgical suture needle through suture holes 160, located on one extension 162a of an elongate arm 162 of implant unit 110, through tissue of the subject, and through surgical mesh 1050 provided on a second extension 162b of elongate arm 162 of implant unit 110. In this embodiment, the larger target area provided by surgical mesh 1050 may facilitate the suturing process because it may be more difficult to precisely locate a suture needle after passing it through tissue. Implantantation and suturing procedures may be further facilitated through the use of a delivery tool, described in greater detail below. The capsules of implant unit 110 may be provided such that implant unit 110 remains flexible after encapsulation. Additionally, implant unit 110 may include meandering electrical traces 1060 in order to maintain electrical contact under flexural conditions. As used herein, meandering electrical traces 1060 may include any electrical trace that is longer than the shortest distance between the points that it connects. Meandering electrical traces 1060 may also include any trace of sufficient length so as to maintain electrical conductivity during flexing of a carrier on which it is located. For example, as shown in FIG. 10, meandering electrical traces 1060 may be configured as lines having successive curves, such as waves or the like. Repeated flexing of carrier 161 on which electrical traces are deposited may cause degradation of the electrical traces, as they are repeatedly stressed with the flexure of carrier 161. Meandering electrical traces 1060 may provide an increased lifetime, as the additional slack provided may serve to reduce stress in the traces during flexing of carrier 161. Meandering electrical traces 1060 may include any suitable conductive material, such as gold, platinum, titanium, copper, silver, iridium, platinum-iridium, platinum-gold, conductive polymers, any conductive biocompatible material, and/or combinations of conductive (and/or noble metals) materials.

In additional embodiments consistent with the present disclosure, conductive electrical elements of implant unit 110, such as meandering traces 1060 and electrodes 158a, 158b may be provided through a progressive metallization layering method. In some embodiments, flexible carrier 161 may include a material, such as liquid crystal polymer, that bonds relatively weakly to conductive metals desirable for use as conductive electrical elements, such as titanium and/or gold. A progressive metallization layering method may utilize a temporary bonding layer, including a metal, such as nickel, that may bond more strongly to flexible carrier 161. The temporary bonding layer may be layered with the metals desirable for use as conductive electrical elements and used to provide an initial bond with the material of flexible carrier 161. The temporary bonding layer may then be removed through dissolution, erosion, or similar technique, through flexible carrier 161, leaving the desirable metals in place in flexible carrier 161.

In one embodiment, a progressive metallization layering method may be utilized to provide gold and titanium conductive elements on a liquid crystal polymer carrier 161. The conductive elements may be constructed from progressive layers of nickel, gold, and titanium. Next, liquid crystal polymer may be molded around the conductive elements, bonding strongly with the nickel layer and forming a recess containing the layered conductive element. Finally, the nickel may be removed through the liquid crystal polymer through dissolution, erosion, or similar technique. The removal of nickel leaves the gold/titanium layered conductive element in place, held tightly in the liquid crystal polymer recess created during the molding process.

Returning to FIGS. 2 and 3, external unit 120 may be configured to communicate with implant unit 110. For example, in some embodiments, a primary signal may be generated on primary antenna 150, using, e.g., processor 144, signal source 142, and amplifier 146. More specifically, in one embodiment, power source 140 may be configured to provide power to one or both of the processor 144 and the signal source 142. The processor 144 may be configured to cause signal source 142 to generate a signal (e.g., an RF energy signal). Signal source 142 may be configured to output the generated signal to amplifier 146, which may amplify the signal generated by signal source 142. The amount of amplification and, therefore, the amplitude of the signal may be controlled, for example, by processor 144. The amount of gain or amplification that processor 144 causes amplifier 146 to apply to the signal may depend on a variety of factors, including, but not limited to, the shape, size, and/or configuration of primary antenna 150, the size of the patient, the location of implant unit 110 in the patient, the shape, size, and/or configuration of secondary antenna 152, a degree of coupling between primary antenna 150 and secondary antenna 152 (discussed further below), a desired magnitude of electric field to be generated by implant electrodes 158a, 158b, etc. Amplifier 146 may output the amplified signal to primary antenna 150.

External unit 120 may communicate a primary signal on primary antenna 150 to the secondary antenna 152 of implant unit 110. This communication may result from coupling between primary antenna 150 and secondary antenna 152. Such coupling of the primary antenna 150 and the secondary antenna 152 may include any interaction between the primary antenna 150 and the secondary antenna 152 that causes a signal on the secondary antenna 152 in response to a signal applied to the primary antenna 150. In some embodiments, coupling between the primary and secondary antennas 150, 152 may include capacitive coupling, inductive coupling, radiofrequency coupling, etc. and any combinations thereof.

Coupling between primary antenna 150 and secondary antenna 152 may depend on the proximity of the primary antenna 150 relative to the secondary antenna 152. That is, in some embodiments, an efficiency or degree of coupling between primary antenna 150 and secondary antenna 152 may depend on the proximity of the primary antenna 150 to the secondary antenna 152. The proximity of the primary and secondary antennas 150, 152 may be expressed in terms of a coaxial offset (e.g., a distance between the primary and secondary antennas when central axes of the primary and secondary antennas are co-aligned), a lateral offset (e.g., a distance between a central axis of the primary antenna and a central axis of the secondary antenna), and/or an angular offset (e.g., an angular difference between the central axes of the primary and secondary antennas). In some embodiments, a theoretical maximum efficiency of coupling may exist between primary antenna 150 and secondary antenna 152 when both the coaxial offset, the lateral offset, and the angular offset are zero. Increasing any of the coaxial offset, the lateral offset, and the angular offset may have the effect of reducing the efficiency or degree of coupling between primary antenna 150 and secondary antenna 152.

As a result of coupling between primary antenna 150 and secondary antenna 152, a secondary signal may arise on secondary antenna 152 when the primary signal is present on the primary antenna 150. Such coupling may include inductive/magnetic coupling, RF coupling/transmission, capacitive coupling, or any other mechanism where a secondary signal may be generated on secondary antenna 152 in response to a primary signal generated on primary antenna 150. Coupling may refer to any interaction between the primary and secondary antennas. In addition to the coupling between primary antenna 150 and secondary antenna 152, circuit components associated with implant unit 110 may also affect the secondary signal on secondary antenna 152. Thus, the secondary signal on secondary antenna 152 may refer to any and all signals and signal components present on secondary antenna 152 regardless of the source.

While the presence of a primary signal on primary antenna 150 may cause or induce a secondary signal on secondary antenna 152, the coupling between the two antennas may also lead to a coupled signal or signal components on the primary antenna 150 as a result of the secondary signal present on secondary antenna 152. A signal on primary antenna 150 induced by a secondary signal on secondary antenna 152 may be referred to as a primary coupled signal component. The primary signal may refer to any and all signals or signal components present on primary antenna 150, regardless of source, and the primary coupled signal component may refer to any signal or signal component arising on the primary antenna 150 as a result of coupling with signals present on secondary antenna 152. Thus, in some embodiments, the primary coupled signal component may contribute to the primary signal on primary antenna 150.

Implant unit 110 may be configured to respond to external unit 120. For example, in some embodiments, a primary signal generated on primary coil 150 may cause a secondary signal on secondary antenna 152, which in turn, may cause one or more responses by implant unit 110. In some embodiments, the response of implant unit 110 may include the generation of an electric field between implant electrodes 158a and 158b.

FIG. 6 illustrates circuitry 170 that may be included in external unit 120 and circuitry 180 that may be included in implant unit 110. Additional, different, or fewer circuit components may be included in either or both of circuitry 170 and circuitry 180. As shown in FIG. 6, secondary antenna 152 may be arranged in electrical communication with implant electrodes 158a, 158b. In some embodiments, circuitry connecting secondary antenna 152 with implant electrodes 158a and 158b may cause a voltage potential across implant electrodes 158a and 158b in the presence of a secondary signal on secondary antenna 152. This voltage potential may be referred to as a field inducing signal, as this voltage potential may generate an electric field between implant electrodes 158a and 158b. More broadly, the field inducing signal may include any signal (e.g., voltage potential) applied to electrodes associated with the implant unit that may result in an electric field being generated between the electrodes.

Energy transfer between primary antenna 150 and secondary antenna 152 via the primary signal may be improved when a resonant frequency of primary antenna 150 and its associated circuitry 170 matches that of secondary antenna 152 and its associated circuitry 180. As used herein a resonant frequency match between two antennas may be characterized by the proximity of two resonant frequencies to one another. For example, a resonant frequency match may be considered to occur when two resonant frequencies are within 30%, 20%, 10%, 5%, 3%, 1%, 0.5%, 0.1%, or less of each other. Accordingly, a resonant frequency mismatch may be considered to occur when two resonant frequencies do not match. The proximity of the two resonant frequencies required to be considered a match may depend on the circumstances of energy transfer between the two antennas. A resonant frequency match between two antennas may also be characterized by the efficiency of energy transfer between the antennas. The efficiency of energy transfer between two antennas may depend on several factors, one of which may be the degree to which the resonant frequencies of the antennas match. Thus, if all other factors are held constant, changing the resonant frequency of one antenna with respect to the other will alter the efficiency of energy transfer. A resonant frequency match between two antennas may be considered to occur when the efficiency of energy transfer is within 50% or greater of a maximum energy transfer when all other factors remain constant. In some embodiments, a resonant frequency match may require energy transfer efficiencies of 60%, 70%, 80%, 90%, 95% or greater.

Several embodiments are provided in order to appropriately match resonant frequencies between a primary signal and a secondary antenna 152. Because the secondary antenna 152 is intended for implantation with implant unit 110, it may be difficult to adjust the resonant frequency of the antenna during use. Furthermore, due to the possibility of moisture incursion into primary capsule 1201 encapsulating implant unit 110, implant circuitry 180, and secondary antenna 152, a resonant frequency of the implant unit 110 may drift after implantation. Other factors present during implantation may also influence the frequency drift of implant unit 110 after implantation. This drifting of the resonant frequency may last for several days to several months after implantation before stabilizing. For example, the resonant frequency of an implant unit 110 may drift from 8.1 kHz to 7.9 kHz. Through experimentation or simulation, it may be possible to predict by how much the resonant frequency may drift. Thus, using the example above, if a long term resonant frequency value of 7.9 kHz is desired, an implant unit 110 may be manufactured with a resonant frequency value of 8.1 kHz prior to implantation.

Resonant frequency values of manufactured implant units 110 may be adjusted during the manufacturing process through the use of at least one trimming capacitor. In one embodiment, carrier 161 may be manufactured with all or some of the components of the final implant unit, including, for example, secondary antenna 152, implant circuitry 180, modulation electrodes 158a, 158b. The resonant frequency of this assembly may then be measured or otherwise determined. Due to variations in manufacturing processes and materials, the resonant frequency of each manufactured unit may differ. Thus, in order to meet a specific resonance frequency, each implant unit may be adjusted through the addition of one or more trimming capacitors to the implant circuitry 180 prior to encapsulation. In one embodiment, a capacitor may be laser trimmed to an exact capacitance value before insertion into implant circuitry 180. In another embodiment, a stock capacitor of known value may be inserted into implant circuitry 180. In still another embodiment, a plurality of capacitors may be inserted into implanted circuitry 180 to appropriately adjust the resonant frequency of implant unit 110. Such a plurality of capacitors may include a series of capacitors having progressively smaller capacitance values, and a resonant frequency of the assembly may be measured after the insertion of each capacitor prior to choosing and inserting the next. In this fashion, implantable circuit 180 may include at least one capacitor configured to create a predetermined mismatch between a resonant frequency of implantable circuit 180 and external circuit 170.

In addition to resonant frequency drift in implant unit 110, a resonant frequency of primary antenna 152 may be altered due to the application of the antenna 152 to the skin of a subject. That is, when primary antenna 152 is bent to conform to the skin of a subject, the spatial relationship coils within primary antenna 152 may shift, causing a change in resonant frequency. In order to address this, a processor 144 of the external unit may be configured to determine a resonant frequency mismatch between primary antenna 152 and secondary antenna 150, and adjust a resonant frequency of primary antenna 152 in order to reduce or eliminate the resonant frequency mismatch. During transmission of a primary signal from primary antenna 150 to secondary antenna 152, processor 144 may be configured to determine a resonant frequency mismatch based on a primary coupled signal component present on the primary antenna 150 due to coupling between primary antenna 152 and secondary antenna 150. Monitoring a primary coupled signal component by the processor 144 may provide an indication of transmission efficiency, which may in turn be an indication of resonant frequency mismatch. The primary coupled signal component and the interaction between primary antenna 152 and secondary antenna 150 are explained in greater detail below.

Upon determining a resonant frequency mismatch between a primary antenna 150 and a secondary antenna 152, processor 144 may adjust the resonant frequency of a self-resonant transmitter circuit including the primary antenna to reduce the mismatch. A self-resonant transmitter circuit may include features to permit adjustment of a resonant frequency of the circuit. Such adjustment may be performed, for example through the selective inclusion and exclusion of at least one capacitor into or out of a self-resonant transmitter circuit. Adding (or subtracting) capacitors to the self-resonant transmitter circuit may cause a change in the resonant frequency of the circuit. In the currently described embodiment, the self-resonant transmitter circuit may be provided with one or more trim capacitors configured, through processor 144 controlled switches, for selective inclusion and exclusion. The switches may include, for example, transistors or relays. Thus, processor 144 may include or exclude a capacitor from the self-resonant transmitter circuit by opening or closing a switch associated with the respective capacitor. Providing a single capacitor, therefore, permits processor 144 to switch the resonant frequency of the self-resonant transmitter circuit between two different values. In an exemplary embodiment, a bank of six capacitors may be provided, permitting processor 144 to switch the resonant frequency of the self-resonant transmitter circuit between 64 (i.e., $2^6$) different values. In alternative embodiments, more or fewer capacitors may be provided for adjusting the resonant frequency of the self-resonant transmitter circuit.

In an exemplary embodiment, processor 144 may be configured to switch capacitors from a capacitor bank into and out of the self-resonant transmitter circuit during transmission of a primary signal to determine a capacitor combination that changes (e.g., increases) transmission efficiency and resonant frequency match. In some embodiments, processor 144 may be configured to select an optimal combination of capacitors to provide a best resonant frequency match. In alternative embodiments, processor 144 may be configured to select a combination of capacitors that provides a resonant frequency match surpassing a predetermined threshold, regardless of whether such combination produces an optimal resonant frequency match.

Resonant frequency matching between primary antenna 150 and secondary antenna 152 may increase the efficiency of energy transfer between the antennas. In further embodiments processor 144 may be configured to adjust the operation of elements within external unit 120 to match a frequency of a primary signal with a resonant frequency of primary antenna 150.

Figure 16:
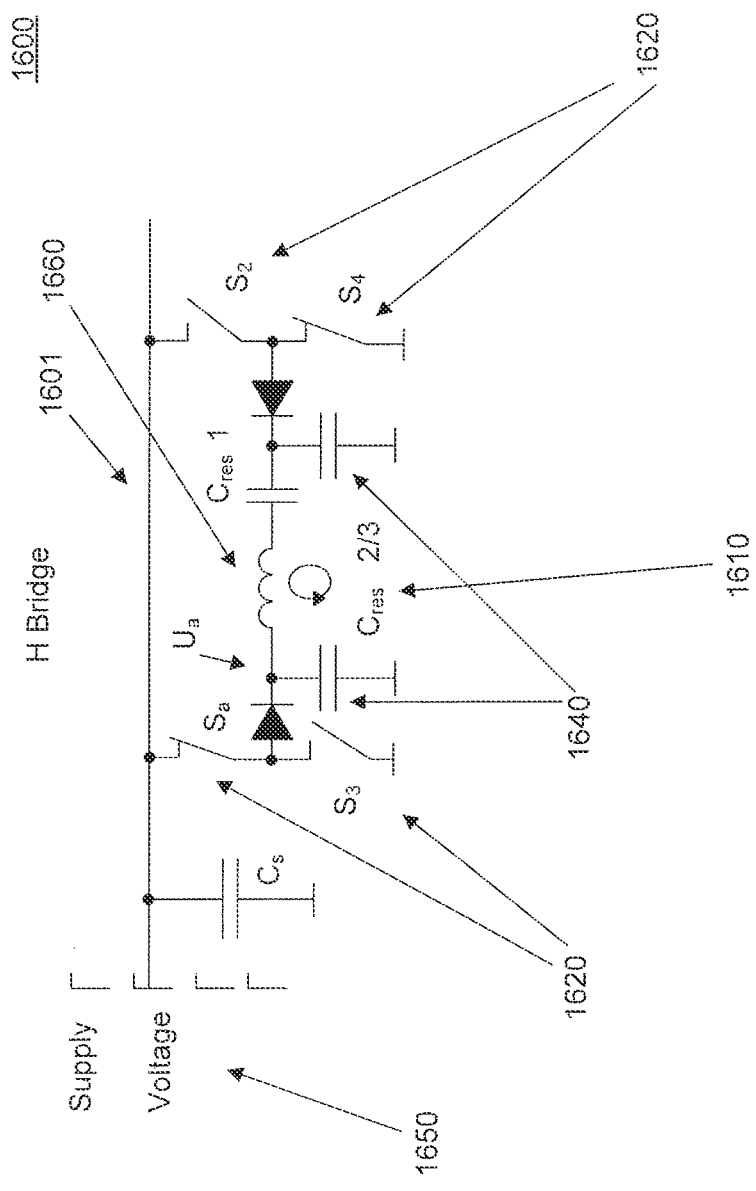
FIG. 16 depicts a self-resonant transmitter employing a modified class D amplifier.

FIG. 16 depicts an additional embodiment illustrating a self-resonant transmitter circuit employing a modified class D amplifier for use with resonant frequency matching methods. Modified class D amplifier 1600 may be used in place of, or in addition to, any or all of the elements of external unit 120 depicted in FIG. 3. For example, modified class D amplifier 1600 may replace signal source 142 and amplifier 146. In this embodiment, processor 144 may be configured to adjust the operation of a class D amplifier to provide a frequency match between a generated signal and a resonant frequency of a primary antenna 150. Because the resonant frequency of primary antenna 150 may be adjusted to match that of secondary antenna 152 during operation, it may be beneficial to adjust the frequency of the generated signal as well to improve efficiency within the self-resonant transmitter circuit of an external unit 120. Modified class D amplifier 1600 may be used to provide such an adjustment as follows. Modified class D amplifier 1600 includes an H bridge 1601 including switches (such as MOSFETs) 1620. Between the switches is self-resonant transmitter circuit 1610. Power to the modified class D amplifier is supplied by supply voltage 1650, which may be supplied from a battery, for example. As shown in FIG. 16, self-resonant transmitter circuit 1610 may include multiple capacitances 1640 and inductances 1660. Capacitances 1640 may include multiple capacitors, combinations of which may be chosen from among trim capacitors as described above, in order to selectively provide an appropriate value of capacitance 1640. The value of capacitance 1640 may be selected for resonant frequency matching to secondary antenna 152. Inductances 1660 may be provided at least partially by primary antenna 150. Processor 144 may also adjust a driving frequency of the H bridge switches 1620 in order to generate a signal of a frequency that matches the resonant frequency of self-resonant circuit 1610. By selectively opening and closing switches 1620 appropriately, the DC signal of supply voltage 1650 may be converted into a square wave of a selected frequency. This frequency may be selected to match the resonant frequency of self-resonant circuit 1610 in order to increase the efficiency of the circuit.

Figure 17:
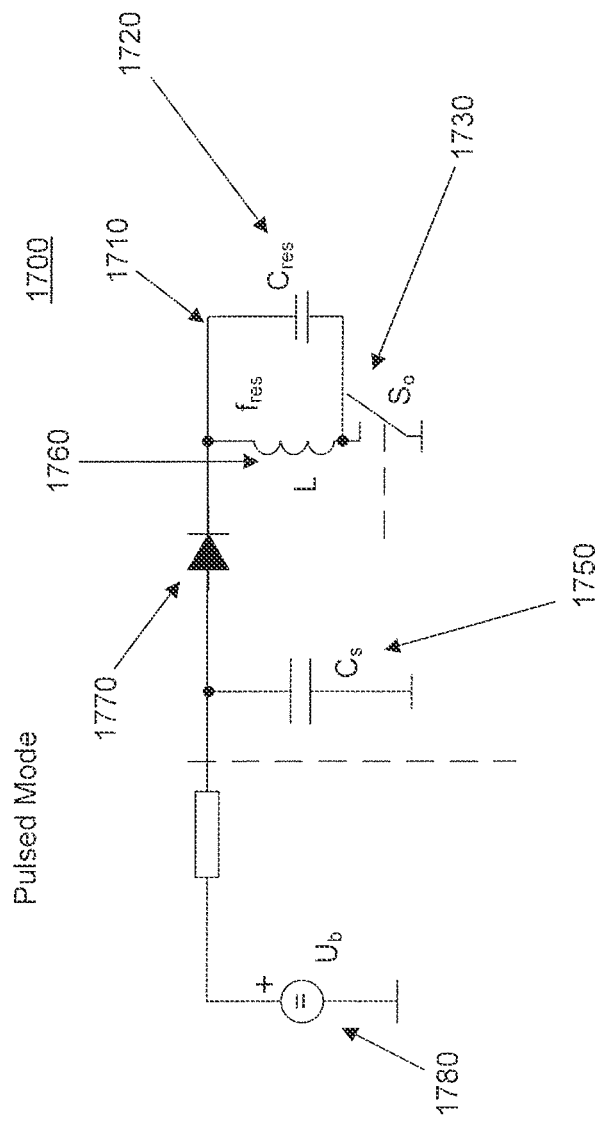
FIG. 17 depicts a pulsed mode self-resonant transmitter.

FIG. 17 depicts an additional embodiment illustrating a pulsed mode self-resonant transmitter 1700 for use with resonant frequency matching methods. Pulsed mode self-resonant transmitter 1700 may be used in place of, or in addition to, any or all of the elements of external unit 120 depicted in FIG. 3. For example, pulsed mode self-resonant transmitter 1700 may replace signal source 142 and amplifier 146. In this embodiment, processor 144 may be configured to control the circuit through a power switching unit, depicted in the present embodiment as switch 1730. A power switching unit may include a transistor, relay, or similar switching device. Pulsed mode self-resonant transmitter 1700 may include a primary power source 1780, for example, a battery or alternative source of power. Transmitter 1700 may include a power storage unit, such as storage capacitor 1750. Other suitable power storage units may also be utilized, such as an inductor and/or battery, as well as combinations of these storage elements. Transmitter 1700 may also include a self-resonant transmitter circuit 1710, including resonance capacitance 1720 and a resonance inductance 1760. Resonance inductance 1760 may be provided at least partially by primary antenna 150.

Transmitter 1700 may operate in the following manner, among others. For example, processor 144 may control the operation of switch 1730. When switch 1730 is maintained in an open position, current from power source 1780 may flow into storage capacitor 1750, which may thereby accumulate an electrical charge. When switch 1730 is closed, charged storage capacitor 1750 may drive current into the self-resonant circuit 1710 during a current loading period, where energy may be stored in inductance 1760. Due to the operation of diode 1770, current flow into circuit 1710 may be cut off after a period of energy accumulation. The current transferred to circuit 1710 may then oscillate freely within circuit 1710 at the resonant frequency of circuit 1710, and thus generate a signal for transmission to the implant through primary antenna 150 (which is included in the circuit and creates at least a portion of inductance 1760). Because the signal is generated by the self resonance of circuit 1710, it will match the resonant frequency of circuit 1710 and a more efficient transmission may be created.

Components of transmitter 1700 may be chosen such that the current loading period may be approximately two microseconds and a period of free oscillation in circuit 1710 may be between 10 and 20 microseconds. Other components may be selected, however, to provide any desired current loading period or free oscillation period. As described elsewhere in this disclosure, stimulation pulses of varying lengths may be desired. Stimulation pulses of longer than a single period of free oscillation may be constructed by multiple cycles of loading and releasing energy from storage capacitor 1750 into circuit 1710. Storage capacitor 1750 may itself be chosen to store enough charge to drive a large number of oscillation cycles (e.g. between 10 and 100) in order to construct entire stimulation pulses without requiring recharging from power source 1780.

Pulsed mode self-resonant transmitter 1700 may provide several advantages. As described above, because the transmission signal is generated by the self-resonance of circuit 1710, it likely will match the resonant frequency of circuit 1710, obviating a need to match the frequency of the generated signal with the circuit resonance frequency. Further, because energy is stored in capacitor 1750 prior to discharge into circuit 1710, a greater flexibility in choice of power source 1780 may be provided. Effective neural stimulation may depend on current levels that rise rapidly. To achieve this with a battery alone may require a high-voltage and/or high-current battery. This need may be obviated by transmitter 1700, which permits the delivery of a very high peak current through the use of a relatively low voltage/low current battery. Transmitter 1700 may use fewer switches (e.g. transistors) than does a conventional amplifying circuit. Each switch may be a source of energy loss, contributing to an overall less efficient circuit. The presence of a single switch 1730 in transmitter 1700 may increase the efficiency of the circuit as a whole.

The field inducing signal may be generated as a result of conditioning of the secondary signal by circuitry 180. As shown in FIG. 6, circuitry 170 of external unit 120 may be configured to generate an AC primary signal on primary antenna 150 that may cause an AC secondary signal on secondary antenna 152. In certain embodiments, however, it may be advantageous (e.g., in order to generate a unidirectional electric field for modulation of a nerve) to provide a DC field inducing signal at implant electrodes 158a and 158b. To convert the AC secondary signal on secondary antenna 152 to a DC field inducing signal, circuitry 180 in implant unit 110 may include an AC-DC converter. The AC to DC converter may include any suitable converter known to those skilled in the art. For example, in some embodiments the AC-DC converter may include rectification circuit components including, for example, diode 156 and appropriate capacitors and resistors. In alternative embodiments, implant unit 110 may include an AC-AC converter, or no converter, in order to provide an AC field inducing signal at implant electrodes 158a and 158b.

As noted above, the field inducing signal may be configured to generate an electric field between implant electrodes 158a and 158b. In some instances, the magnitude and/or duration of the generated electric field resulting from the field inducing signal may be sufficient to modulate one or more nerves in the vicinity of electrodes 158a and 158b. In such cases, the field inducing signal may be referred to as a modulation signal. In other instances, the magnitude and/or duration of the field inducing signal may generate an electric field that does not result in nerve modulation. In such cases, the field inducing signal may be referred to as a sub-modulation signal.

Various types of field inducing signals may constitute modulation signals. For example, in some embodiments, a modulation signal may include a moderate amplitude and moderate duration, while in other embodiments, a modulation signal may include a higher amplitude and a shorter duration. Various amplitudes and/or durations of field-inducing signals across electrodes 158a, 158b may result in modulation signals, and whether a field-inducing signal rises to the level of a modulation signal can depend on many factors (e.g., distance from a particular nerve to be stimulated; whether the nerve is branched; orientation of the induced electric field with respect to the nerve; type of tissue present between the electrodes and the nerve; etc.).

Whether a field inducing signal constitutes a modulation signal (resulting in an electric field that may cause nerve modulation) or a sub-modulation signal (resulting in an electric field not intended to cause nerve modulation) may ultimately be controlled by processor 144 of external unit 120. For example, in certain situations, processor 144 may determine that nerve modulation is appropriate. Under these conditions, processor 144 may cause signal source 144 and amplifier 146 to generate a modulation control signal on primary antenna 150 (i.e., a signal having a magnitude and/or duration selected such that a resulting secondary signal on secondary antenna 152 will provide a modulation signal at implant electrodes 158a and 158b).

Processor 144 may be configured to limit an amount of energy transferred from external unit 120 to implant unit 110. For example, in some embodiments, implant unit 110 may be associated with a threshold energy limit that may take into account multiple factors associated with the patient and/or the implant. For example, in some cases, certain nerves of a patient should receive no more than a predetermined maximum amount of energy to minimize the risk of damaging the nerves and/or surrounding tissue. Additionally, circuitry 180 of implant unit 110 may include components having a maximum operating voltage or power level that may contribute to a practical threshold energy limit of implant unit 110. Processor 144 may be configured to account for such limitations when setting the magnitude and/or duration of a primary signal to be applied to primary antenna 150.

In addition to determining an upper limit of power that may be delivered to implant unit 110, processor 144 may also determine a lower power threshold based, at least in part, on an efficacy of the delivered power. The lower power threshold may be computed based on a minimum amount of power that enables nerve modulation (e.g., signals having power levels above the lower power threshold may constitute modulation signals while signals having power levels below the lower power threshold may constitute sub-modulation signals).

A lower power threshold may also be measured or provided in alternative ways. For example, appropriate circuitry or sensors in the implant unit 110 may measure a lower power threshold. A lower power threshold may be computed or sensed by an additional external device, and subsequently programmed into processor 144, or programmed into implant unit 110. Alternatively, implant unit 110 may be constructed with circuitry 180 specifically chosen to generate signals at the electrodes of at least the lower power threshold. In still another embodiment, an antenna of external unit 120 may be adjusted to accommodate or produce a signal corresponding to a specific lower power threshold. The lower power threshold may vary from patient to patient, and may take into account multiple factors, such as, for example, modulation characteristics of a particular patient's nerve fibers, a distance between implant unit 110 and external unit 120 after implantation, and the size and configuration of implant unit components (e.g., antenna and implant electrodes), etc.

Processor 144 may also be configured to cause application of sub-modulation control signals to primary antenna 150. Such sub-modulation control signals may include an amplitude and/or duration that result in a sub-modulation signal at electrodes 158a, 158b. While such sub-modulation control signals may not result in nerve modulation, such sub-modulation control signals may enable feedback-based control of the nerve modulation system. That is, in some embodiments, processor 144 may be configured to cause application of a sub-modulation control signal to primary antenna 150. This signal may induce a secondary signal on secondary antenna 152, which, in turn, may induce a primary coupled signal component on primary antenna 150.

To analyze the primary coupled signal component induced on primary antenna 150, external unit 120 may include feedback circuit 148 (e.g., a signal analyzer or detector, etc.), which may be placed in direct or indirect communication with primary antenna 150 and processor 144. Sub-modulation control signals may be applied to primary antenna 150 at any desired periodicity. In some embodiments, the sub-modulation control signals may be applied to primary antenna 150 at a rate of one every five seconds (or longer). In other embodiments, the sub-modulation control signals may be applied more frequently (e.g., once every two seconds, once per second, once per millisecond, once per nanosecond, or multiple times per second). Further, it should be noted that feedback may also be received upon application of modulation control signals to primary antenna 150 (i.e., those that result in nerve modulation), as such modulation control signals may also result in generation of a primary coupled signal component on primary antenna 150.

The primary coupled signal component may be fed to processor 144 by feedback circuit 148 and may be used as a basis for determining a degree of coupling between primary antenna 150 and secondary antenna 152. The degree of coupling may enable determination of the efficacy of the energy transfer between two antennas. Processor 144 may also use the determined degree of coupling in regulating delivery of power to implant unit 110.

Processor 144 may be configured with any suitable logic for determining how to regulate power transfer to implant unit 110 based on the determined degree of coupling. For example, where the primary coupled signal component indicates that a degree of coupling has changed from a baseline coupling level, processor 144 may determine that secondary antenna 152 has moved with respect to primary antenna 150 (either in coaxial offset, lateral offset, or angular offset, or any combination). Such movement, for example, may be associated with a movement of the implant unit 110, and the tissue that it is associated with based on its implant location. Thus, in such situations, processor 144 may determine that modulation of a nerve in the patient's body is appropriate. More particularly, in response to an indication of a change in coupling, processor 144, in some embodiments, may cause application of a modulation control signal to primary antenna 150 in order to generate a modulation signal at implant electrodes 158a, 158b, e.g., to cause modulation of a nerve of the patient.

In an embodiment for the treatment of OSA, movement of an implant unit 110 may be associated with movement of the tongue, which may indicate the onset of a sleep apnea event or a sleep apnea precursor. The onset of a sleep apnea event or sleep apnea precursor may require the stimulation of the genioglossus muscle of the patient to relieve or avert the event. Such stimulation may result in contraction of the muscle and movement of the patient's tongue away from the patient's airway.

In embodiments for the treatment of head pain, including migraines, processor 144 may be configured to generate a modulation control signal based on a signal from a user, for example, or a detected level of neural activity in a sensory neuron (e.g. the greater occipital nerve or trigeminal nerve) associated with head pain. A modulation control signal generated by the processor and applied to the primary antenna 150 may generate a modulation signal at implant electrodes 158a, 158b, e.g., to cause inhibition or blocking of a sensory nerve of the patient. Such inhibition or blocking may decrease or eliminate the sensation of pain for the patient.

In embodiments for the treatment of hypertension, processor 144 may be configured to generate a modulation control signal based on, for example, pre-programmed instructions and/or signals from an implant indicative of blood pressure. A modulation control signal generated by the processor and applied to the primary antenna 150 may generate a modulation signal at implant electrodes 158a, 158b, e.g., to cause either inhibition or stimulation of nerve of a patient, depending on the requirements. For example, a neuromodulator placed in a carotid artery or jugular artery (i.e. in the vicinity of a carotid baroreceptor), may receive a modulation control signal tailored to induce a stimulation signal at the electrodes, thereby causing the glossopharyngeal nerve associated with the carotid baroreceptors to fire at an increased rate in order to signal the brain to lower blood pressure. Similar modulation of the glossopharyngeal nerve may be achieved with a neuromodulator implanted in a subcutaneous location in a patient's neck or behind a patient's ear. A neuromodulator place in a renal artery may receive a modulation control signal tailored to cause an inhibiting or blocking signal at the electrodes, thereby inhibiting a signal to raise blood pressure carried from the renal nerves to the kidneys.

Modulation control signals may include stimulation control signals, and sub-modulation control signals may include sub-stimulation control signals. Stimulation control signals may have any amplitude, pulse duration, or frequency combination that results in a stimulation signal at electrodes 158a, 158b. In some embodiments (e.g., at a frequency of between about 6.5-13.6 MHz), stimulation control signals may include a pulse duration of greater than about 50 microseconds and/or an amplitude of approximately 0.5 amps, or between 0.1 amps and 1 amp, or between 0.05 amps and 3 amps. Sub-stimulation control signals may have a pulse duration less than about 500, or less than about 200 nanoseconds and/or an amplitude less than about 1 amp, 0.5 amps, 0.1 amps, 0.05 amps, or 0.01 amps. Of course, these values are meant to provide a general reference only, as various combinations of values higher than or lower than the exemplary guidelines provided may or may not result in nerve stimulation.

In some embodiments, stimulation control signals may include a pulse train, wherein each pulse includes a plurality of sub-pulses. An alternating current signal (e.g., at a frequency of between about 6.5-13.6 MHz) may be used to generate the pulse train, as follows. A sub-pulse may have a duration of between 50-250 microseconds, or a duration of between 1 microsecond and 2 milliseconds, during which an alternating current signal is turned on. For example, a 200 microsecond sub-pulse of a 10 MHz alternating current signal will include approximately 2000 periods. Each pulse may, in turn, have a duration of between 100 and 500 milliseconds, during which sub-pulses occur at a frequency of between 25 and 100 Hz. For example, a 200 millisecond pulse of 50 Hz sub-pulses will include approximately 10 sub-pulses. Finally, in a pulse train, each pulse may be separated from the next by a duration of between 0.2 and 2 seconds. For example, in a pulse train of 200 millisecond pulses, each separated by 1.3 seconds from the next, a new pulse will occur every 1.5 seconds. A pulse train of this embodiment may be utilized, for example, to provide ongoing stimulation during a treatment session. In the context of OSA, a treatment session may be a period of time during which a subject is asleep and in need of treatment to prevent OSA. Such a treatment session may last anywhere from about three to ten hours. In the context of other conditions to which neural modulators of the present disclosure are applied, a treatment session may be of varying length according to the duration of the treated condition.

Processor 144 may be configured to determine a degree of coupling between primary antenna 150 and secondary antenna 152 by monitoring one or more aspects of the primary coupled signal component received through feedback circuit 148. In some embodiments, processor 144 may determine a degree of coupling between primary antenna 150 and secondary antenna 152 by monitoring a voltage level associated with the primary coupled signal component, a current level, or any other attribute that may depend on the degree of coupling between primary antenna 150 and secondary antenna 152. For example, in response to periodic sub-modulation signals applied to primary antenna 150, processor 144 may determine a baseline voltage level or current level associated with the primary coupled signal component. This baseline voltage level, for example, may be associated with a range of movement of the patient's tongue when a sleep apnea event or its precursor is not occurring, e.g. during normal breathing. As the patient's tongue moves toward a position associated with a sleep apnea event or its precursor, the coaxial, lateral, or angular offset between primary antenna 150 and secondary antenna 152 may change. As a result, the degree of coupling between primary antenna 150 and secondary antenna 152 may change, and the voltage level or current level of the primary coupled signal component on primary antenna 150 may also change. Processor 144 may be configured to recognize a sleep apnea event or its precursor when a voltage level, current level, or other electrical characteristic associated with the primary coupled signal component changes by a predetermined amount or reaches a predetermined absolute value.

Figure 7:
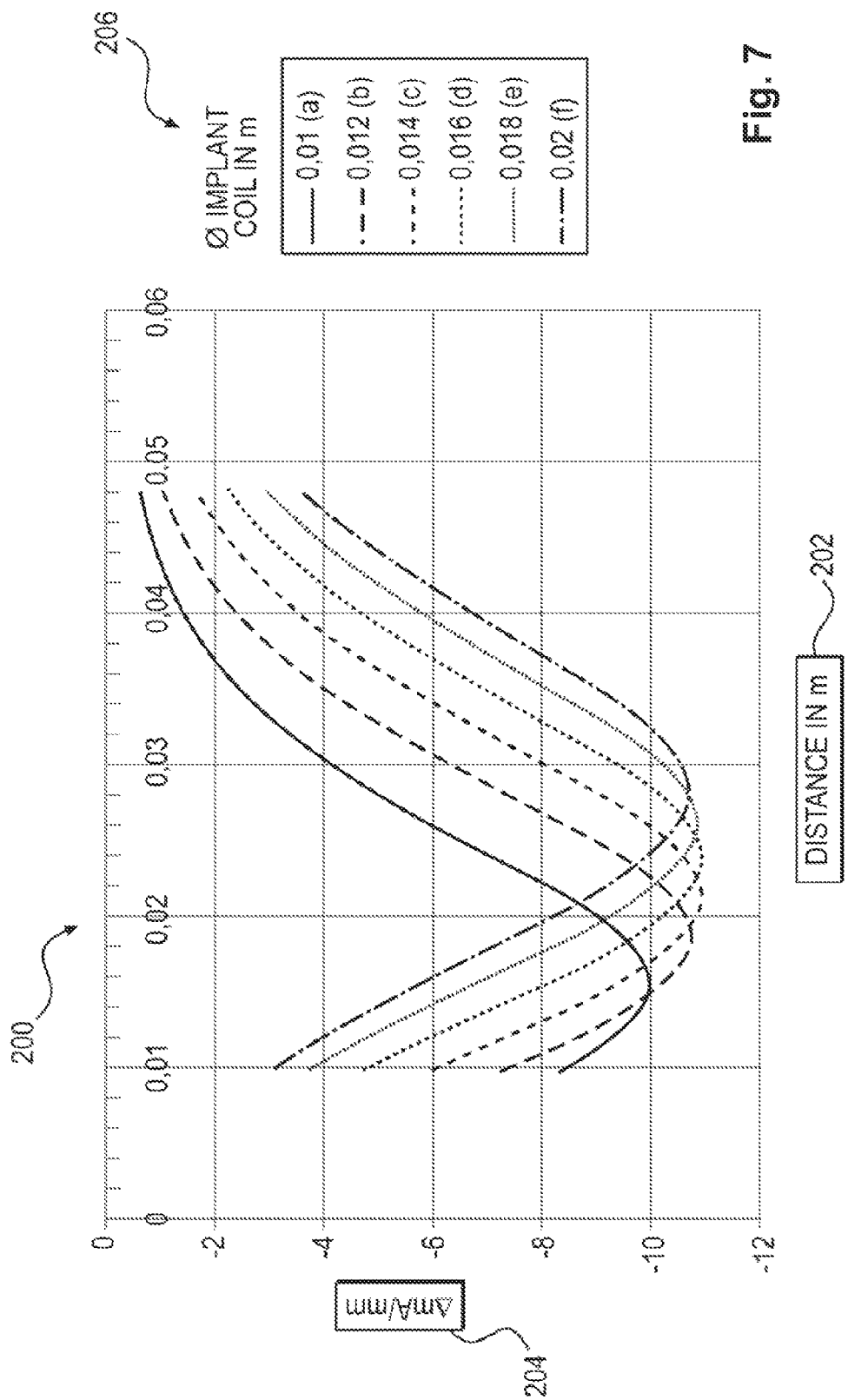
FIG. 7 illustrates a graph of quantities that may be used in determining energy delivery as a function coupling, according to an exemplary disclosed embodiment.

FIG. 7 provides a graph that illustrates this principle in more detail. For a two-coil system where one coil receives a radio frequency (RF) drive signal, graph 200 plots a rate of change in induced current in the receiving coil as a function of coaxial distance between the coils. For various coil diameters and initial displacements, graph 200 illustrates the sensitivity of the induced current to further displacement between the coils, moving them either closer together or further apart. It also indicates that, overall, the induced current in the secondary coil will decrease as the secondary coil is moved away from the primary, drive coil, i.e. the rate of change of induced current, in mA/mm, is consistently negative. The sensitivity of the induced current to further displacement between the coils may vary with distance. For example, at a separation distance of 10 mm, the rate of change in current as a function of additional displacement in a 14 mm coil is approximately −6 mA/mm. If the displacement of the coils is approximately 22 mm, the rate of change in the induced current in response to additional displacement is approximately −11 mA/mm, which corresponds to a local maximum in the rate of change of the induced current. Increasing the separation distance beyond 22 mm continues to result in a decline in the induced current in the secondary coil, but the rate of change decreases. For example, at a separation distance of about 30 mm, the 14 mm coil experiences a rate of change in the induced current in response to additional displacement of about −8 mA/mm. With this type of information, processor 144 may be able to determine a particular degree of coupling between primary antenna 150 and secondary antenna 152, at any given time, by observing the magnitude and/or rate of change in the magnitude of the current associated with the primary coupled signal component on primary antenna 150.

Processor 144 may be configured to determine a degree of coupling between primary antenna 150 and secondary antenna 152 by monitoring other aspects of the primary coupled signal component. For example, in some embodiments, the non-linear behavior of circuitry 180 in implant unit 110 may be monitored to determine a degree of coupling. For example, the presence, absence, magnitude, reduction and/or onset of harmonic components in the primary coupled signal component on primary antenna 150 may reflect the behavior of circuitry 180 in response to various control signals (either sub-modulation or modulation control signals) and, therefore, may be used to determine a degree of coupling between primary antenna 150 and secondary antenna 152.

As shown in FIG. 6, circuitry 180 in implant unit 110 may constitute a non-linear circuit due, for example, to the presence of non-linear circuit components, such as diode 156. Such non-linear circuit components may induce non-linear voltage responses under certain operation conditions. Non-linear operation conditions may be induced when the voltage potential across diode 156 exceeds the activation threshold for diode 156. Thus, when implant circuitry 180 is excited at a particular frequency, this circuit may oscillate at multiple frequencies. Spectrum analysis of the secondary signal on secondary antenna 152, therefore, may reveal one or more oscillations, called harmonics, that appear at certain multiples of the excitation frequency. Through coupling of primary antenna 150 and secondary antenna 152, any harmonics produced by implant circuitry 180 and appearing on secondary antenna 152 may also appear in the primary coupled signal component present on primary antenna 150.

In certain embodiments, circuitry 180 may include additional circuit components that alter the characteristics of the harmonics generated in circuitry 180 above a certain transition point. Monitoring how these non-linear harmonics behave above and below the transition point may enable a determination of a degree of coupling between primary antenna 150 and secondary antenna 152. For example, as shown in FIG. 6, circuitry 180 may include a harmonics modifier circuit 154, which may include any electrical components that non-linearly alter the harmonics generated in circuitry 180. In some embodiments, harmonics modifier circuit 154 may include a pair of Zener diodes. Below a certain voltage level, these Zener diodes remain forward biased such that no current will flow through either diode. Above the breakdown voltage of the Zener diodes, however, these devices become conductive in the reversed biased direction and will allow current to flow through harmonics modifier circuit 154. Once the Zener diodes become conductive, they begin to affect the oscillatory behavior of circuitry 180, and, as a result, certain harmonic oscillation frequencies may be affected (e.g., reduced in magnitude).

Figure 8:
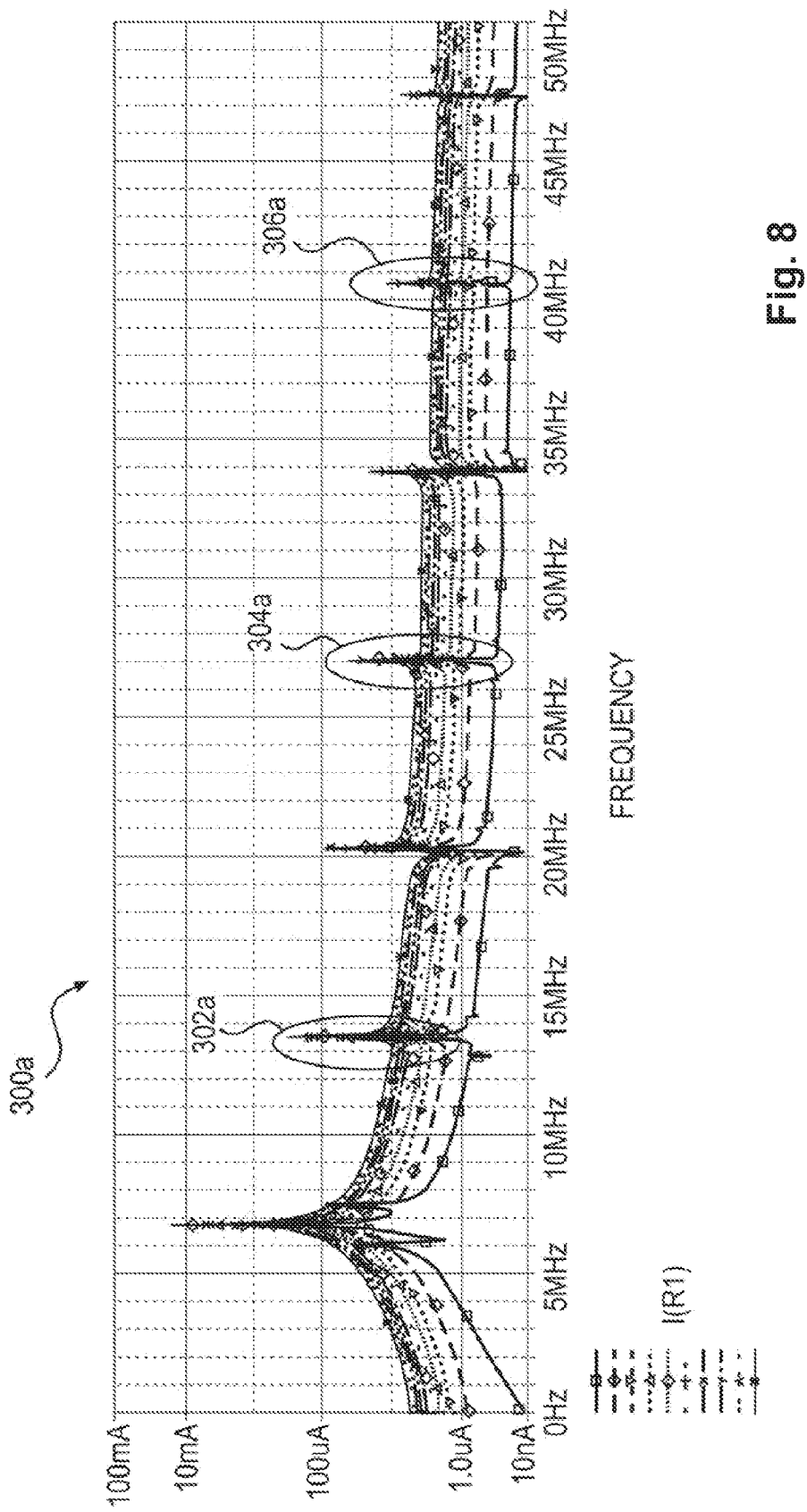
FIG. 8 depicts a graph illustrating non-linear harmonics.
Figure 9:
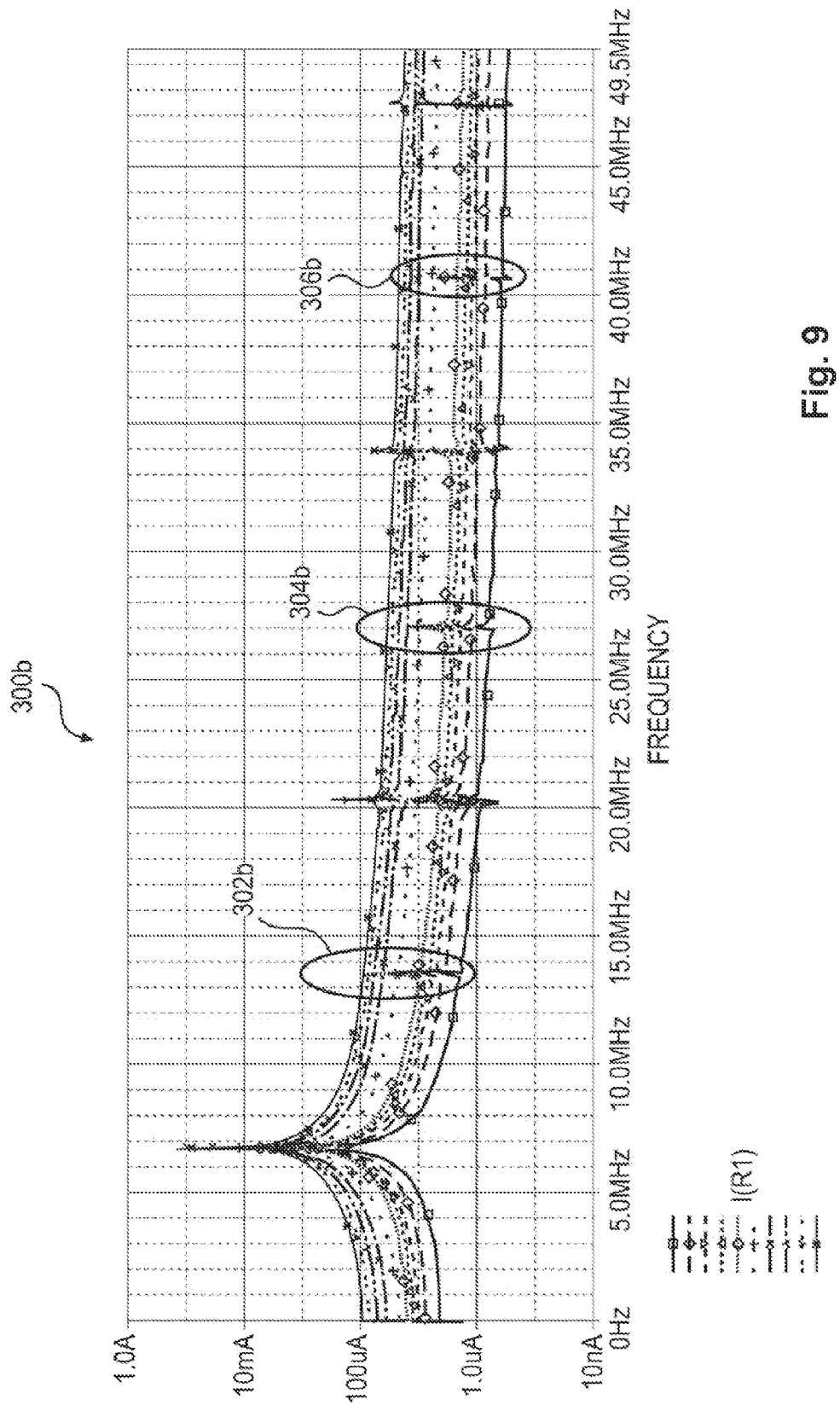
FIG. 9 depicts a graph of quantities that may be used in determining energy delivery as a function coupling, according to an exemplary disclosed embodiment.

FIGS. 8 and 9 illustrate this effect. For example, FIG. 8 illustrates a graph 300a that shows the oscillatory behavior of circuitry 180 at several amplitudes ranging from about 10 nanoamps to about 20 microamps. As shown, the primary excitation frequency occurs at about 6.7 MHz and harmonics appear both at even and odd multiples of the primary excitation frequency. For example, even multiples appear at twice the excitation frequency (peak 302a), four times the excitation frequency (peak 304a) and six times the excitation frequency (peak 306a). As the amplitude of the excitation signal rises between 10 nanoamps and 40 microamps, the amplitude of peaks 302a, 304a, and 306a all increase.

FIG. 9 illustrates the effect on the even harmonic response of circuitry 180 caused by harmonics modifier circuit 154. FIG. 9 illustrates a graph 300b that shows the oscillatory behavior of circuitry 180 at several amplitudes ranging from about 30 microamps to about 100 microamps. As in FIG. 8, FIG. 9 shows a primary excitation frequency at about 6.7 MHz and second, fourth, and sixth order harmonics (peaks 302b, 304b, and 306b, respectively) appearing at even multiples of the excitation frequency. As the amplitude of the excitation signal rises, however, between about 30 microamps to about 100 microamps, the amplitudes of peaks 302b, 304b, and 306b do not continuously increase. Rather, the amplitude of the second order harmonics decreases rapidly above a certain transition level (e.g., about 80 microamps in FIG. 8). This transition level corresponds to the level at which the Zener diodes become conductive in the reverse biased direction and begin to affect the oscillatory behavior of circuitry 180.

Monitoring the level at which this transition occurs may enable a determination of a degree of coupling between primary antenna 150 and secondary antenna 152. For example, in some embodiments, a patient may attach external unit 120 over an area of the skin under which implant unit 110 resides. Processor 144 can proceed to cause a series of sub-modulation control signals to be applied to primary antenna 150, which in turn cause secondary signals on secondary antenna 152. These sub-modulation control signals may progress over a sweep or scan of various signal amplitude levels. By monitoring the resulting primary coupled signal component on primary antenna 150 (generated through coupling with the secondary signal on secondary antenna 152), processor 144 can determine the amplitude of primary signal (whether a sub-modulation control signal or other signal) that results in a secondary signal of sufficient magnitude to activate harmonics modifier circuit 154. That is, processor 144 can monitor the amplitude of the second, fourth, or sixth order harmonics and determine the amplitude of the primary signal at which the amplitude of any of the even harmonics drops. FIGS. 8 and 9 illustrate the principles of detecting coupling through the measurement of non-linear harmonics. These Figs illustrate data based around a 6.7 MHz excitation frequency. These principles, however, are not limited to the 6.7 MHz excitation frequency illustrated, and may be used with a primary signal of any suitable frequency.

In some embodiments, the determined amplitude of the primary signal corresponding to the transition level of the Zener diodes (which may be referred to as a primary signal transition amplitude) may establish a baseline range when the patient attaches external unit 120 to the skin. Presumably, while the patient is awake, the tongue is not blocking the patient's airway and moves with the patients breathing in a natural range, where coupling between primary antenna 150 and secondary antenna 152 may be within a baseline range. A baseline coupling range may encompass a maximum coupling between primary antenna 150 and secondary antenna 152. A baseline coupling range may also encompass a range that does not include a maximum coupling level between primary antenna 150 and secondary antenna 152. Thus, the initially determined primary signal transition amplitude may be fairly representative of a non-sleep apnea condition and may be used by processor 144 as a baseline in determining a degree of coupling between primary antenna 150 and secondary antenna 152. Optionally, processor 144 may also be configured to monitor the primary signal transition amplitude over a series of scans and select the minimum value as a baseline, as the minimum value may correspond to a condition of maximum coupling between primary antenna 150 and secondary antenna 152 during normal breathing conditions.

As the patient wears external unit 120, processor 144 may periodically scan over a range of primary signal amplitudes to determine a current value of the primary signal transition amplitude. In some embodiments, the range of amplitudes that processor 144 selects for the scan may be based on (e.g., near) the level of the baseline primary signal transition amplitude. If a periodic scan results in determination of a primary signal transition amplitude different from the baseline primary signal transition amplitude, processor 144 may determine that there has been a change from the baseline initial conditions. For example, in some embodiments, an increase in the primary signal transition amplitude over the baseline value may indicate that there has been a reduction in the degree of coupling between primary antenna 150 and secondary antenna 152 (e.g., because the implant has moved or an internal state of the implant has changed).

In addition to determining whether a change in the degree of coupling has occurred, processor 144 may also be configured to determine a specific degree of coupling based on an observed primary signal transition amplitude. For example, in some embodiments, processor 144 may have access to a lookup table or a memory storing data that correlates various primary signal transition amplitudes with distances (or any other quantity indicative of a degree of coupling) between primary antenna 150 and secondary antenna 152. In other embodiments, processor 144 may be configured to calculate a degree of coupling based on performance characteristics of known circuit components.

By periodically determining a degree of coupling value, processor 144 may be configured to determine, in situ, appropriate parameter values for the modulation control signal that will ultimately result in nerve modulation. For example, by determining the degree of coupling between primary antenna 150 and secondary antenna 152, processor 144 may be configured to select characteristics of the modulation control signal (e.g., amplitude, pulse duration, frequency, etc.) that may provide a modulation signal at electrodes 158a, 158b in proportion to or otherwise related to the determined degree of coupling. In some embodiments, processor 144 may access a lookup table or other data stored in a memory correlating modulation control signal parameter values with degree of coupling. In this way, processor 144 may adjust the applied modulation control signal in response to an observed degree of coupling.

Additionally or alternatively, processor 144 may be configured to determine the degree of coupling between primary antenna 150 and secondary antenna 152 during modulation. The tongue, or other structure on or near which the implant is located, and thus implant unit 110, may move as a result of modulation. Thus, the degree of coupling may change during modulation. Processor 144 may be configured to determine the degree of coupling as it changes during modulation, in order to dynamically adjust characteristics of the modulation control signal according to the changing degree of coupling. This adjustment may permit processor 144 to cause implant unit 110 to provide an appropriate modulation signal at electrodes 158a, 158b throughout a modulation event. For example, processor 144 may alter the primary signal in accordance with the changing degree of coupling in order to maintain a constant modulation signal, or to cause the modulation signal to be reduced in a controlled manner according to patient needs.

More particularly, the response of processor 144 may be correlated to the determined degree of coupling. In situations where processor 144 determines that the degree of coupling between primary antenna 150 and secondary antenna has fallen only slightly below a predetermined coupling threshold (e.g, during snoring or during a small vibration of the tongue or other sleep apnea event precursor), processor 144 may determine that only a small response is necessary. Thus, processor 144 may select modulation control signal parameters that will result in a relatively small response (e.g., a short stimulation of a nerve, small muscle contraction, etc.). Where, however, processor 144 determines that the degree of coupling has fallen substantially below the predetermined coupling threshold (e.g., where the tongue has moved enough to cause a sleep apnea event), processor 144 may determine that a larger response is required. As a result, processor 144 may select modulation control signal parameters that will result in a larger response. In some embodiments, only enough power may be transmitted to implant unit 110 to cause the desired level of response. In other words, processor 144 may be configured to cause a metered response based on the determined degree of coupling between primary antenna 150 and secondary antenna 152. As the determined degree of coupling decreases, processor 144 may cause transfer of power in increasing amounts. Such an approach may preserve battery life in the external unit 120, may protect circuitry 170 and circuitry 180, may increase effectiveness in addressing the type of detected condition (e.g., sleep apnea, snoring, tongue movement, etc.), and may be more comfortable for the patient.

In some embodiments, processor 144 may employ an iterative process in order to select modulation control signal parameters that result in a desired response level. For example, upon determining that a modulation control signal should be generated, processor 144 may cause generation of an initial modulation control signal based on a set of predetermined parameter values. If feedback from feedback circuit 148 indicates that a nerve has been modulated (e.g, if an increase in a degree of coupling is observed), then processor 144 may return to a monitoring mode by issuing sub-modulation control signals. If, on the other hand, the feedback suggests that the intended nerve modulation did not occur as a result of the intended modulation control signal or that modulation of the nerve occurred but only partially provided the desired result (e.g, movement of the tongue only partially away from the airway), processor 144 may change one or more parameter values associated with the modulation control signal (e.g., the amplitude, pulse duration, etc.).

Where no nerve modulation occurred, processor 144 may increase one or more parameters of the modulation control signal periodically until the feedback indicates that nerve modulation has occurred. Where nerve modulation occurred, but did not produce the desired result, processor 144 may re-evaluate the degree of coupling between primary antenna 150 and secondary antenna 152 and select new parameters for the modulation control signal targeted toward achieving a desired result. For example, where stimulation of a nerve causes the tongue to move only partially away from the patient's airway, additional stimulation may be desired. Because the tongue has moved away from the airway, however, implant unit 110 may be closer to external unit 120 and, therefore, the degree of coupling may have increased. As a result, to move the tongue a remaining distance to a desired location may require transfer to implant unit 110 of a smaller amount of power than what was supplied prior to the last stimulation-induced movement of the tongue. Thus, based on a newly determined degree of coupling, processor 144 can select new parameters for the stimulation control signal aimed at moving the tongue the remaining distance to the desired location.

In one mode of operation, processor 144 may be configured to sweep over a range of parameter values until nerve modulation is achieved. For example, in circumstances where an applied sub-modulation control signal results in feedback indicating that nerve modulation is appropriate, processor 144 may use the last applied sub-modulation control signal as a starting point for generation of the modulation control signal. The amplitude and/or pulse duration (or other parameters) associated with the signal applied to primary antenna 150 may be iteratively increased by predetermined amounts and at a predetermined rate until the feedback indicates that nerve modulation has occurred.

Processor 144 may be configured to determine or derive various physiologic data based on the determined degree of coupling between primary antenna 150 and secondary antenna 152. For example, in some embodiments the degree of coupling may indicate a distance between external unit 120 and implant unit 110, which processor 144 may use to determine a position of external unit 120 or a relative position of a patient's tongue. Monitoring the degree of coupling can also provide such physiologic data as whether a patient's tongue is moving or vibrating (e.g, whether the patient is snoring), by how much the tongue is moving or vibrating, the direction of motion of the tongue, the rate of motion of the tongue, etc.

In response to any of these determined physiologic data, processor 144 may regulate delivery of power to implant unit 110 based on the determined physiologic data. For example, processor 144 may select parameters for a particular modulation control signal or series of modulation control signals for addressing a specific condition relating to the determined physiologic data. If the physiologic data indicates that the tongue is vibrating, for example, processor 144 may determine that a sleep apnea event is likely to occur and may issue a response by delivering power to implant unit 110 in an amount selected to address the particular situation. If the tongue is in a position blocking the patient's airway (or partially blocking a patient's airway), but the physiologic data indicates that the tongue is moving away from the airway, processor 144 may opt to not deliver power and wait to determine if the tongue clears on its own. Alternatively, processor 144 may deliver a small amount of power to implant unit 110 (e.g., especially where a determined rate of movement indicates that the tongue is moving slowly away from the patient's airway) to encourage the tongue to continue moving away from the patient's airway or to speed its progression away from the airway. The scenarios described are exemplary only. Processor 144 may be configured with software and/or logic enabling it to address a variety of different physiologic scenarios with particularity. In each case, processor 144 may be configured to use the physiologic data to determine an amount of power to be delivered to implant unit 110 in order to modulate nerves associated with the tongue with the appropriate amount of energy.

The disclosed embodiments may be used in conjunction with a method for regulating delivery of power to an implant unit. The method may include determining a degree of coupling between primary antenna 150 associated with external unit 120 and secondary antenna 152 associated with implant unit 110, implanted in the body of a patient. Determining the degree of coupling may be accomplished by processor 144 located external to implant unit 110 and that may be associated with external unit 120. Processor 144 may be configured to regulate delivery of power from the external unit 120 to the implant unit 110 based on the determined degree of coupling.

As previously discussed, the degree of coupling determination may enable the processor to further determine a location of the implant unit. The motion of the implant unit may correspond to motion of the body part where the implant unit may be attached. This may be considered physiologic data received by the processor. The processor may, accordingly, be configured to regulate delivery of power from the power source to the implant unit based on the physiologic data. In alternative embodiments, the degree of coupling determination may enable the processor to determine information pertaining to a condition of the implant unit. Such a condition may include location as well as information pertaining to an internal state of the implant unit. The processor may, according to the condition of the implant unit, be configured to regulate delivery of power from the power source to the implant unit based on the condition data.

In some embodiments, implant unit 110 may include a processor located on the implant. A processor located on implant unit 110 may perform all or some of the processes described with respect to the at least one processor associated with an external unit. For example, a processor associated with implant unit 110 may be configured to receive a control signal prompting the implant controller to turn on and cause a modulation signal to be applied to the implant electrodes for modulating a nerve. Such a processor may also be configured to monitor various sensors associated with the implant unit and to transmit this information back to external unit 120. Power for the processor unit may be supplied by an onboard power source or received via transmissions from an external unit.

In other embodiments, implant unit 110 may be self-sufficient, including its own power source and a processor configured to operate the implant unit 110 with no external interaction. For example, with a suitable power source, the processor of implant unit 110 may be configured to monitor conditions in the body of a subject (via one or more sensors or other means), determining when those conditions warrant modulation of a nerve, and generate a signal to the electrodes to modulate a nerve. The power source could be regenerative based on movement or biological function; or the power sources could be periodically rechargeable from an external location, such as, for example, through induction.

Figure 14:
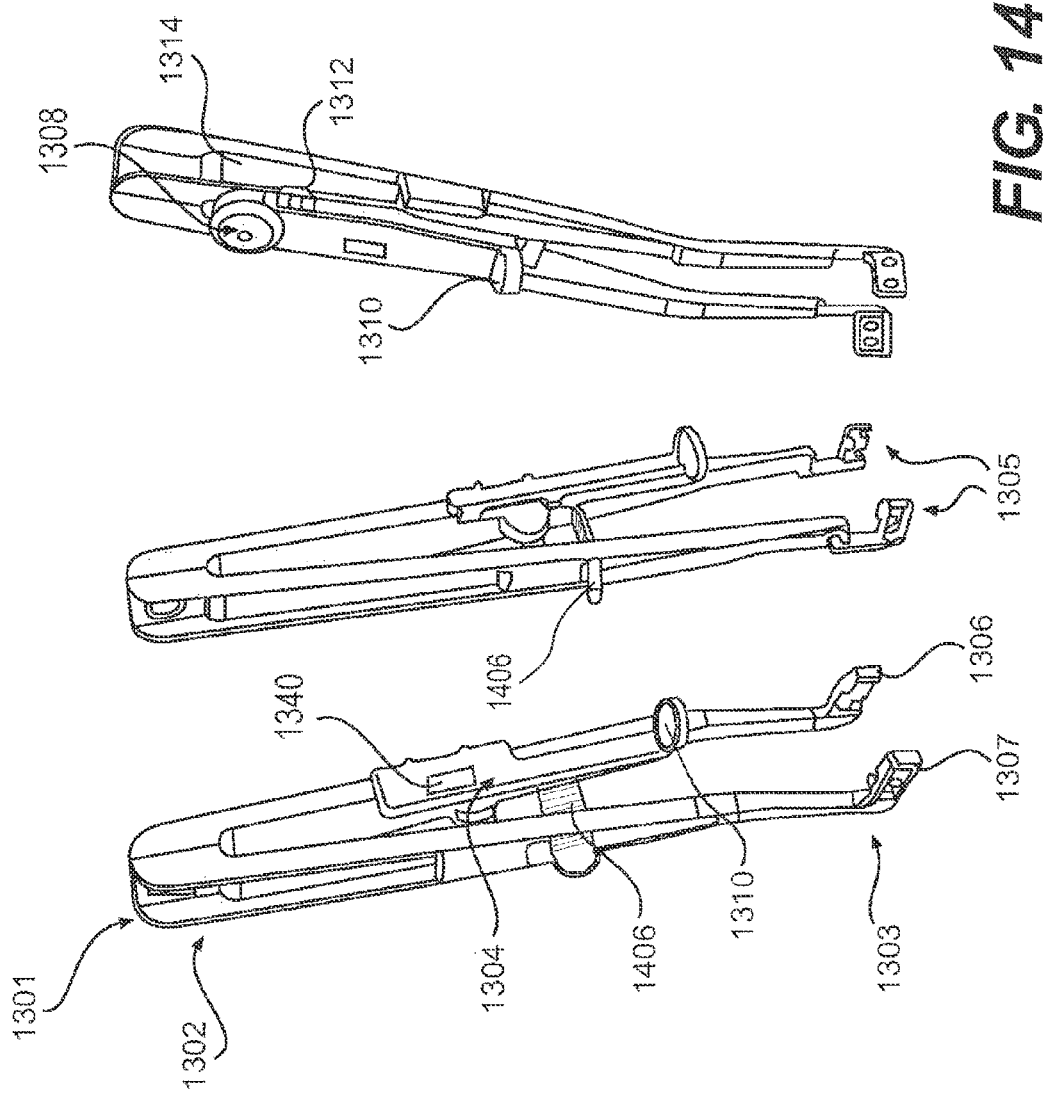
FIG. 14 illustrates various aspects of a delivery tool.
Figure 15:
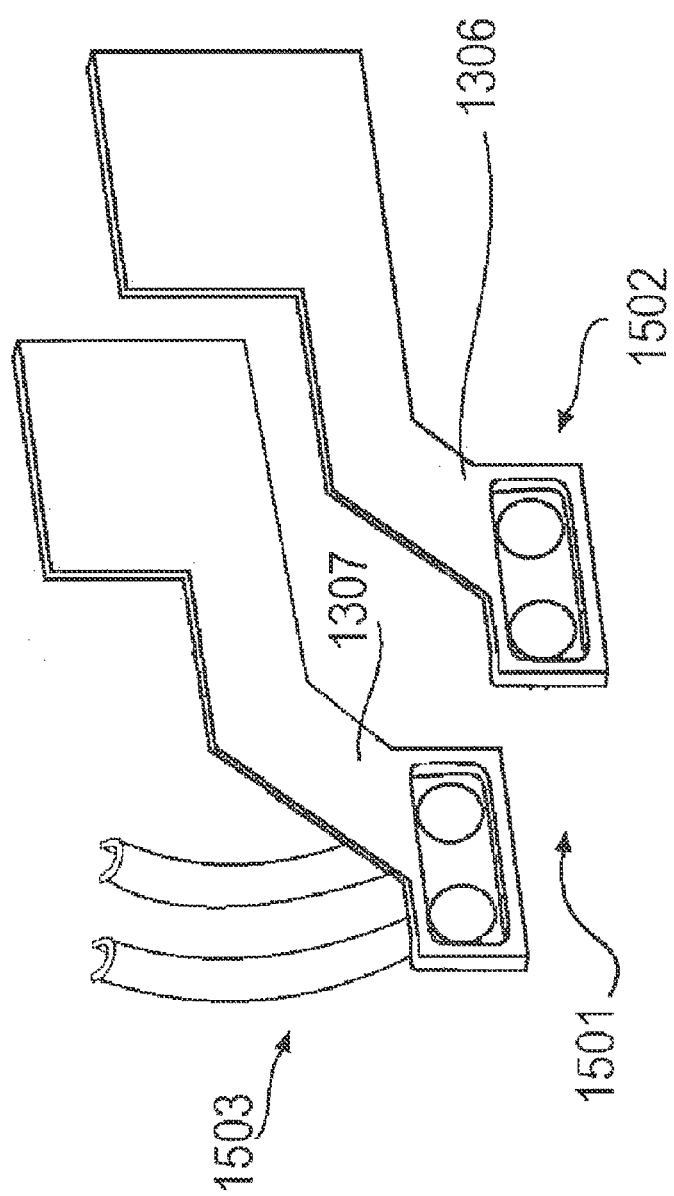
FIG. 15 depicts features of a delivery tool implant holder portion.

Some embodiments of the present disclosure may include methods, devices, and tools for the implantation of implant unit 110. FIGS. 13-15 illustrate an exemplary embodiment of a delivery tool for use in the implantation of implant unit 110 and various features thereof. The features illustrated in FIGS. 13-15 may be combined in any suitable fashion in various embodiments consistent with this disclosure. A delivery tool 1301 may be used during an implantation procedure to properly position implant unit 110, to test implant unit 110, and/or to assist a surgeon in securing implant unit 110 to an appropriate internal body structure.

FIGS. 13a-13b illustrate various aspects of delivery tool 1301. In some embodiments, delivery tool 1301 may include an implant retainer configured to selectively hold implant unit 110 and maintain implant unit 110 in a fixation location relative to target tissue in a subject's body during an implantation procedure. Delivery tool 1301 may include a body 1302, an implant holder 1303 adapted to releasably hold an implant unit, an implant activator 1304, and a power source 1308 associated with the implant activator 1304. Body 1302 may include a handle formed so as to receive a thumb and at least one forefinger of a user. As shown in FIG. 13a, body 1302 may include a first face 1315 and a second face 1316. Holder 1303 may include any structure adapted to hold and release an implant unit. In some embodiments, holder 1303 may be adapted to hold implant unit 110. Holder 1303 may include various components to releasably hold implant unit 110, such as a vacuum element (not shown), or latching element (not shown), etc.

Holder 1303 may also include a pair of jaws 1305 disposed in an opposing relationship as shown in FIG. 13c. For example, jaws 1305 may include a first jaw 1306 pivotally attached to a second jaw 1307. The spacing of the opposing jaws 1305 may be adjustable, for example through a tweezer-type movement of the delivery tool 1301. The tweezer-type movement of the delivery tool 1301 may be controlled by a ratchet 1406, as shown in FIG. 14, configured to maintain spacing between jaws 1305 when employed. Thus, a user may position implant unit 110 inside jaws 1305, press the jaws 1305 together until implant unit 110 is firmly held in a flexed position, and employ ratchet 1406 to maintain the spacing of jaws 1305. A user, such as a surgeon, may then release pressure on the delivery tool 1301 while the position of the implant unit 110 is maintained with ratchet 1406. Maintaining a position of the implant unit may be useful prior to an implantation procedure, as a surgeon prepares for the implantation. It may also be useful during an implantation procedure, as a surgeon may hold implant unit 110 in place with respect to an implantation location as implantation steps are performed. Ratchet 1406 may be released, for example when implant unit 110 is within a desired position within the patient, causing jaws 1305 to open. Implant unit 110 may then be released from delivery tool 1301 and implanted within the patient. As shown in FIG. 14, ratchet 1406 may include various configuration as is known in the art.

The flexed position of the implant unit 110, between jaws 1305, may be chosen such that the implant unit 110 may substantially conform to a contour of tissue in a patient's body when implanted. For example, holder 1303 may hold implant unit 110 in a bent, curved, compressed, or stretched configuration. As shown in FIG. 13c, holder 1303 may hold implant unit 110 such that first extension 162a of implant unit 110 is maintained substantially against second jaw 1307 and second extension 162b of implant unit 110 is maintained substantially against first jaw 1306.

Holder 1303 may also include at least one suture guide member 1501, configured to receive surgical sutures. As shown in FIG. 15, a suture guide member 1501 may include a first suture guide portion 1502 and a second suture guide portion 1503 adapted for the insertion and/or guiding of a surgical needle during an implantation process. First suture guide portion 1502 may be disposed on a first side of holder 1303 and second suture guide portion 1503 may be disposed on a second side of holder 1303, wherein the second side is opposite the first side. Therefore, first and second suture guide portions 1502, 1503 may be associated with holder 1303.

First suture guide portion 1502 may include one or more apertures in jaws 1305, and second suture guide portion 1503 may include a curved channel. In one embodiment, first suture guide portion 1502 may include an aperture in first jaw 1306. The channel of second suture guide portion 1503 may include an arcuate shape extending from second jaw 1307. The channel may have a radius of curvature corresponding to a surgical needle. For example, suture guide member 1501 may be shaped so as to receive any type of surgical suture needle, such as ¼ circle, ⅜ circle, ⅝ circle, ½ circle or ½ curved. Suture guide member 1501 may be configured to correspond to suture holes 160 and/or surgical mesh 1050 of implant unit 110, and may thus facilitate an implantation procedure.

During an implantation procedure, implant unit 110 may be positioned to conform to a tissue structure of a subject, and a surgeon may use suture guide member 1501 to appropriately locate and guide a suture needle in order to suture implant unit 110 in place. Suture guide member 1501 may be configured to set a predetermined angle between suture guide member 1501 and a patient's tissue, and therefore may assist the surgeon by permitting the insertion of a suture needle at the predetermined angle. For example, suture guide member 1501 may set an angle of about 90 degrees between suture guide member 1501 and the patient's tissue. In other embodiments, suture guide member 1501 may set an angle of about 60, about 45, or about 30 degrees.

Returning now to FIGS. 13*a-c*, as described above, delivery tool 1301 may include an implant activator 1304. Implant activator 1304 may be configured to be employed and activated during an implantation procedure. Implant activator 1304 may include an activator antenna 1310, at least one processor 1340 in electrical communication with activator antenna 1310, and a power source 1308. Implant activator 1304 may be configured to interact wirelessly with implant unit 110 to cause modulation of at least one nerve in the body of a patient prior to final fixation of implant unit 110 to tissue. In some embodiments, implant activator 1304 may be configured to interact with implant unit 110 through signals transmitted by activator antenna 1310.

Implant activator 1304 may be slideably disposed on delivery tool 1301 such that implant activator 1304 may slide within a track 1314 formed between first and second faces 1315, 1316. Therefore, implant activator 1304 may slide toward and away from an implant 110, disposed between jaws 1305, within track 1314. For example, implant activator 1304 may slide from a first position (FIG. 13*a*) to a second position (FIG. 13*b*) a predetermined distance along body 1302. It is further contemplated that one or more securing means 1317 may secure and retain implant activator 1340 within track 1314 when sliding up and down along body 1302. Additionally or alternatively, a protrusion 1312 on implant activator 1304 may slide within the groove formed by track 1314. Securing means 1317 and/or protrusion 1312 may selectively lock implant activator 1304 at a predetermined location along body 1302.

A slideable engagement portion 1321 may activate implant activator 1304 causing implant activator 1304 to slide from the first position toward the second position or from the second position toward the first position. For example, slideable engagement portion 1321 may include a trigger or button configured to be engaged by a user. In one embodiment, a user may depress slideable engagement portion 1321 to activate implant activator 1304. Alternatively, implant activator 1304 may be moved from the first position to the second position, and from the second position to the first position, through a pivotal movement facilitated by a pivotal attachment (not shown). It is further contemplated that a user may slide implant activator 1304 into the desired position to move implant activator 1304 along track 1314. A shown in FIG. 14, implant activator 1304 may include various shapes and depressions configured to conform to a user's fingers or palm. Such may enable easy sliding of implant activator 1304. Other means of shifting implant activator 1304 may also be employed without departing from the disclosed embodiments.

Processor 1340 may be configured to determine and regulate a degree of coupling between activator antenna 1310 and secondary antenna 152. As shown in FIG. 13*a*, processor 1340 may be located within or on a surface of body 1302 of delivery tool 1301. In alternative embodiments, processor 1340 may be configured for wired or wireless communication from a location external to delivery tool 1301. Processor 1340 may include, for example, one or more integrated circuits, microchips, microcontrollers, and microprocessors, which may be all or part of a central processing unit (CPU), a digital signal processor (DSP), a field programmable gate array (FPGA), or any other circuit known to those skilled in the art that may be suitable for executing instructions or performing logic operations.

Power source 1308 may be removably or permanently coupled to body 1302 of delivery tool 1301. For example, as shown in FIG. 13*a*, power source may be disposed on an outer or inner surface of implant activator 1304. Power source 1308 may in electrical and wireless communication with processor 1340 and activator implant 1310. For example, power source 1308 may be configured to activate various components including activator antenna 1310 and processor 1340 by transferring power to these components. Power source 1308 may include any source of power capable of activating activator antenna 1310 or processor 1340, for example a battery.

Activator antenna 1310 may be in communication with processor 1340 and power source 1308, and configured to interact with and activate secondary antenna 152 on implant 110. Therefore, activator antenna 1310 may be configured to selectively transfer power from power source 1308 to implant unit 110 during an implantation procedure to cause modulation of at least one nerve in the body of a subject prior to final fixation of implant unit 110. Activator antenna 1310 may include any conductive structure configured to create an electromagnetic field. Activator antenna 1310 may be of any suitable size, shape, and/or configuration. The size, shape, and/or configuration may be determined by the size of the patient, the placement location of implant unit 110, the size and/or shape of implant unit 110, the amount of energy required to activate implant unit 110, the type of receiving electronics present on implant unit 110, etc.

Activator antenna 1310 may include any suitable antenna known to those skilled in the art that may be configured to send and/or receive signals. Suitable antennas may include, but are not limited to, a long-wire antenna, a patch antenna, a helical antenna, etc. In one embodiment, for example, activator antenna 1310 may include a coil antenna. Such a coil antenna may be made from any suitable conductive material and may be configured to include any suitable arrangement of conductive coils (e.g., diameter, number of coils, layout of coils, etc.). A coil antenna suitable for use as activator antenna 1310 may have a diameter of between about 0.1 cm and 10 cm, and may be circular or oval shaped, among other suitable shapes. In some embodiments, activator antenna 1310 may have a diameter between 0.5 cm and 2 cm, and may be oval shaped. A coil antenna suitable for use as activator antenna 1310 may have any number of windings, e.g. 4, 8, 12, or more. A coil antenna suitable for use as activator antenna 1310 may have a wire diameter between about 0.01 mm and 2 mm. These antenna parameters are exemplary only, and may be adjusted above or below the ranges given to achieve suitable results. It is further contemplated that activator antenna 1310 may include the same antenna as secondary antenna 152.

During an exemplary implantation procedure, a surgeon may use delivery tool 1301 to position implant unit 110 in a prospective implantation location and may engage jaws 1305 to bend implant unit 110 such that it substantially conforms to the tissue at the prospective implantation location. For example, implant unit 110 may be positioned in an arc shape in holder 1303 such that first suture guide portion 1502 is disposed on a first open end of the arc and second suture guide portion is disposed on a second open end of the arc (FIG. 13c). Therefore, the first open of the arc may be positioned along first jaw 1306 and the second open end of the arc may be positioned along second jaw 1307 of holder 1303. It is further contemplated that delivery tool 1301 may position implant unit 110 in various configurations and positions. In some embodiments, delivery tool 1301 may position implant unit 110 in a configuration that substantially conforms to the tissue at the site of implantation.

The first and second suture guide portions 1502, 1503 may be configured such that the second suture guide portion 1503 may guide a surgical needle after exiting first suture guide portion 1502. Therefore, a user (e.g. surgeon) may pass the surgical needle through first suture guide portion 1502, through implant unit 110, and then through second suture guide portion 1503. The surgical needle may pass through surgical mesh 1050 after exiting first suture guide portion 1502. The curved channel of second suture guide portion 1503 may provide a pathway for the surgical needle, thus allowing a surgeon to follow the pathway when suturing implant 110 with the surgical needle. In some embodiments, surgical needle may include surgical suture to suture implant within a patient. Additionally, it is further contemplated that an automatic suturing unit (not shown) may guide the suture from first suture guide portion 1502 and through the curved channel of second suture guide portion 1503.

A locking mechanism, such as ratchet mechanism 1406 may lock and maintain jaws 1306, 1307 in a fixed position during the implantation of implant unit 110. For example, ratchet mechanism 1406 may secure jaws 1306, 1307 into a suitable position for implant unit 110 to form the arc shape while allowing hands free operation by a user. The locking mechanism may also affix delivery tool 1301 in a fixed position relative to tissue in the body of a subject. For example, the operator may slide jaws 1307, 1307 over a genioglossus muscle in the subject and lock the locking mechanism once a desired location is reached. The implant may then be activated in that location to test for a desired level of nerve modulation and/or muscle contraction. If the location is not suitable, or does not satisfy expectations, the locking mechanism may be disengaged, and the insert tool 1301 may be moved to another location for testing. Therefore, ratchet mechanism may additionally lock and maintain first and second suture guide portions 1502, 1503 into a desired position during the implantation of implant unit 110. Once a suitable location is found, the implant unit may be sutured in place. In some embodiments, one or more automatic sutures may be triggered.

During an implantation procedure, a user may release ratchet mechanism 1406 and reposition implant unit 110 within holder 1303. For example, the user may reposition implant unit 110 to a configuration that more closely conforms to the patient's tissue at the site of implantation. Additionally, a user may release ratchet mechanism 1406 to move implant unit 110 from a first implantation location to a second implantation location.

The implantation location may be a position suitable for nerve modulation. Once at the desired implantation location, a surgeon may then depress slideable engagement portion 1321 and slide implant activator 1304 from the first position as shown in FIG. 13a to the second position as shown in FIG. 13b. Moving the implant activator 1304 from the first position to the second position may have the effect of bringing activator antenna 1310 into proximity with secondary antenna 152 of implant unit 110. When energized in the second position, for example by power source 1308, activator antenna 1310 may transfer power to implant unit 110. In one embodiment, activator antenna 1310 may transfer power to implant unit 110 through, for example, radiofrequency transmission.

An actuator 1320 may be configured to enable power transmission between activator antenna 1310 and secondary antenna 152 to test the functionality of implant unit 110. As shown in FIG. 13b, actuator 1320 may include a trigger or button disposed on body 1302 of delivery tool 1301. In other embodiments, actuator 1320, may refer to any device that activates the power sent to the implant activator. For example, actuator 1320 may include a switch, with an on/off position, disposed on body 1302 of delivery tool 1301. Actuator 1320 may be positioned such that a user (e.g. surgeon) may engage the switch and move it to an "on" position to deliver power to implant activator 1304. In some embodiments, implant activator 1304 may only activate secondary antenna 1310 when actuator 1320 is in the "on" position. Actuator 1320 may act as a safety barrier to prevent any accidental activation of implant activator 1304. In some embodiments, actuator 1320 may be located outside delivery tool 1301 and may include, for example, a cable to be connected with the implant activator.

After shifting the implant activator from the first position to the second position, a user may enable power transmission between activator antenna 1310 and secondary antenna 152 of implant unit 110 to test the functionality of implant unit 110. This may occur prior to final fixation of implant unit 110 to the patient's tissue. Once activated by implant activator 1304, implant unit 110 may be tested via feedback received by implant activator 1304, for example feedback received by processor 1340. It is contemplated that activator antenna 1310 may receive a feedback signal from secondary antenna 152, and processor 1340 may process the feedback signal. Based on the received feedback signal, processor 1340 may determine if a prospective implant location of implant 110 is sufficient to cause modulation of the subject. For example, processor 1340 may determine that implant unit 110 is not in a sufficient location (e.g. too far) from a desired nerve to properly cause modulation of the nerve.

Additionally or alternatively, implant unit 110 may be tested through one or more patient signals, for example observation of patient response. A surgeon may determine that a prospective implant location is suitable based on whether signals applied to activation modulation electrodes 158a, 158b, of implant unit 110 effectively modulate the patient's nerves. For example, when placing an implant unit 110 for treatment of OSA, a surgeon may determine a prospective implantation location by observing a patient's tongue movement during power transmission. In some embodiments, a surgeon may determine that a first implant location is not suitable, and may move implant unit 110 to a second implant location. The surgeon may then determine that the second implant location is suitable for nerve modulation. After determining that a prospective implantation location constitutes a suitable modulation position, the surgeon may then secure the implant unit 110 in position with sutures, adhesives, clamps, or various other attachment means.

Implant activator 1304 may also be configured to verify the functionality of implant unit 110 prior to the beginning of an implantation procedure. For example, implant activator 1304 may be configured to verify that implant 110 is working properly and able to sufficiently modulate a patient once implanted within the patient. A surgeon may prepare delivery tool 1301 with implant unit 110 as described above (e.g. between jaws 1305), and shift implant activator 1304 from the first position to the second position along body 1302. Implant unit 110 may be shifted to the second position before it is implanted in the patient's body. In this method, the surgeon may then activate implant unit 110 to verify that implant unit 110 does not suffer from manufacturing defects. Implant activator 1304 may use, for example, coupling detection techniques described herein in order to verify the functionality of implant unit 110. A result of such verification may be outputted via an audio output, a visual output, and/or a tactile output, for example.

Other embodiments of the present disclosure will be apparent to those skilled in the art from consideration of the specification and practice of the present disclosure.

Additional aspects of the invention are described in the following numbered paragraphs, which are part of the description of exemplary embodiments of the invention. Each numbered paragraph stands on its own as a separate embodiment of the invention.

What is claimed is:

1. A method of testing the functionality of an implant unit, the method comprising:

moving an implant activator from a first position to a second position on a delivery tool prior to final fixation of an implant unit by the delivery tool, the implant unit being configured for implantation within a body of a subject during a treatment session;

testing the implant unit at an implant location in the body of the subject by transferring power from the implant activator to the implant unit when the implant activator is in the second position, wherein transferring power to the implant unit causes modulation of at least one nerve in the body of the subject;

suturing the implant unit in place at the implant location; and after suturing the implant unit, releasing the implant unit from the delivery tool.

2. The method of claim 1, wherein power is wirelessly transferred from the implant activator to the implant unit.

3. The method of claim 1, wherein the implant activator includes a power source configured to supply the power to the implant unit.

4. The method of claim 3, wherein the power source is a battery.

5. The method of claim 1, wherein the second position is closer to the implant unit than the first position.

6. The method of claim 1, wherein moving the implant activator from the first position to the second position includes sliding the implant activator along a track on the delivery tool.

7. The method of claim 6, further including selectively activating the implant activator and causing the implant activator to move toward and away from the implant unit with a slidable engagement portion.

8. The method of claim 1, further including:

determining that the implant location is suitable based on one or more patient signals; and implanting the implant unit at the location.

9. The method of claim 8, further including:

determining that a first implant location is not suitable based on one or more patient signals; and moving the implant location to a second implant location.

10. The method of claim 1, further including fixing the implant unit in place relative to tissue in the body of the subject.

* * * * *